(12) United States Patent
Rasnetsov et al.

(10) Patent No.: US 9,096,492 B2
(45) Date of Patent: Aug. 4, 2015

(54) HYDRATED N-FULLERENE AMINO ACIDS, METHOD FOR PRODUCING THE LATTER, AND PHARMACEUTICAL COMPOSITIONS ON THE BASIS THEREOF

(75) Inventors: Lev Davidovich Rasnetsov, Nizhny Novgorod (RU); Iakov Yudelevich Shvartsman, Nizhny Novgorod (RU); Olga Nikolaevna Suvorova, Nizhny Novgorod (RU)

(73) Assignee: Lev Davidovich Rasnetsov, Nizhny Novgorod (RU)

( * ) Notice: Subject to any disclaimer, the term of this patent is extended or adjusted under 35 U.S.C. 154(b) by 18 days.

(21) Appl. No.: 13/820,793

(22) PCT Filed: Feb. 6, 2012

(86) PCT No.: PCT/RU2012/000063
§ 371 (c)(1),
(2), (4) Date: Mar. 5, 2013

(87) PCT Pub. No.: WO2012/105873
PCT Pub. Date: Aug. 9, 2012

(65) Prior Publication Data
US 2013/0165692 A1    Jun. 27, 2013

(30) Foreign Application Priority Data
Feb. 1, 2011    (RU) ................................ 2011103541

(51) Int. Cl.
*C07C 229/08* (2006.01)
*C07C 229/12* (2006.01)
*C07C 227/14* (2006.01)
*C07C 229/50* (2006.01)
*C07C 227/18* (2006.01)
*C07C 229/14* (2006.01)

(52) U.S. Cl.
CPC ............. *C07C 229/12* (2013.01); *C07C 227/14* (2013.01); *C07C 227/18* (2013.01); *C07C 229/14* (2013.01); *C07C 229/50* (2013.01)

(58) Field of Classification Search
CPC .................................................. C07C 229/02
USPC ....................................................... 562/565
See application file for complete search history.

(56) References Cited

U.S. PATENT DOCUMENTS 6,204,391 B1    3/2001   Friedman et al.

FOREIGN PATENT DOCUMENTS

RU    2124022 C1    12/1998
RU    2196602 C1    1/2003
RU    2236852 C1    9/2004
RU    2316320 C1    2/2008

OTHER PUBLICATIONS

Partha, et al., "Biomedical applications of functionalized fullerene-based nanomaterials", International Journal of Nanomedicine, 2009, vol. 4, pp. 261-275.
Bakry, R., et al., "Medicinal applications of fullerenes", International Journal of Nanomedicine, 2007, vol. 4, pp. 639-649.
Zhu, Z., et al., "Molecular Dynamics Study of the Connection between Flap Closing and Binding of Fullerene-Based Inhibitors of the HIV-1 Protease", Biochemistry, 2003, vol. 42, pp. 1326-1333.
Bedrov, D., et al., "Passive Transport of $C_{60}$ Fullerenes through a Lipid Membrane: A Molecular Dynamics Simulation Study", J. Phys. Chem. B 200, vol. 112 pp. 2078-2084, Year: 2008.
Qiao R., et al., "Translocation of $C_{60}$ and Its Derivatives Across a Lipid Bilayer", Nano Letters 2007, vol. 7, No. 3, pp. 614-619.
Nielsen, G., et al., "In vivo Biology and toxicology of Fullerenes and Their Derivatives", Basic & Clinical Pharmacology & Toxicology, 2008, vol. 103, pp. 197-208.
Andrievsky, G., et al., "Peculiarities of the antioxidant and radioprotective effects of hydrated $C_{60}$ fullerene nanostructures in vitro and in vivo", Free Radical Biology & Medicine, 2009, vol. 47, pp. 786-793.
Reed, L., et al., "A Simple Method of Estimating Fifty Per Cent Endpoints", The American Journal of Hygiene, May 1938, vol. 27, No. 3, pp. 493-497.
English Abstract RU2236852 C1.
English Abstact RU 2316320 C1.

*Primary Examiner* — Yong Chu
*Assistant Examiner* — Sonya Wright
(74) *Attorney, Agent, or Firm* — Ladas & Parry LLP

(57) ABSTRACT

The invention relates to the pharmaceutical industry and to medicine, specifically to novel hydrated amino-acid derivatives of fullerene $C_{60}$ of general formula $C_{60}(H)_3\{NH(CH_2)_n COOH\}_3 \cdot xH_2O$, where $C_{60}$-fullerene, n=5, 6, 7, x=8-10, and also to a method for producing said derivatives, and to the production of pharmaceutical compositions on the basis thereof. Hydrated N-fullerene amino acids are formed in the interaction of fullerene with 15 times the molar excess of anhydrous potassium salts of amino acids in a medium of organic aromatic solvent with slow addition to the resultant suspension of an interphase catalyst and with mixing and heating to a temperature not exceeding 60° C. until the solution is completely decolorized and a solid residue formed, after which the latter is separated out, and then 0.8 M of aqueous solutions of potassium salts of fullerene amino-acid derivatives is treated with a solution of organic or mineral acids, followed by centrifugation, rinsing and drying of the residue. A pharmaceutical composition which exhibits activity against the herpes virus, flu viruses of various origin and HIV, and also anti-tumor and anti-psoriatic activity, comprising, as active substance, an effective quantity of hydrated N-fullerene amino acids.

4 Claims, No Drawings

HYDRATED N-FULLERENE AMINO ACIDS, METHOD FOR PRODUCING THE LATTER, AND PHARMACEUTICAL COMPOSITIONS ON THE BASIS THEREOF

RELATED APPLICATION INFORMATION

This application is a 371 of International Application PCT/RU2012/000063 filed 6 Feb. 2012 entitled "Hydrated N Fullerene Amino Acids, Method For Producing The Latter, And Pharmaceutical Compositions On The Basis Thereof", which was published on 9 Aug. 2012 with International Publication Number WO 2012/105873 AI, and which claims priority from Russian Patent Applications No.: 2011103541 filed 1 Feb. 2011, the contents of which are incorporated herein by reference.

FIELD OF ART

This invention relates to the pharmaceutical industry and medicine, more specifically, to novel hydrated amino acid derivatives of fullerene $C_{60}$ of formula (I), and to a method for producing same and to making pharmaceutical compositions comprising same.

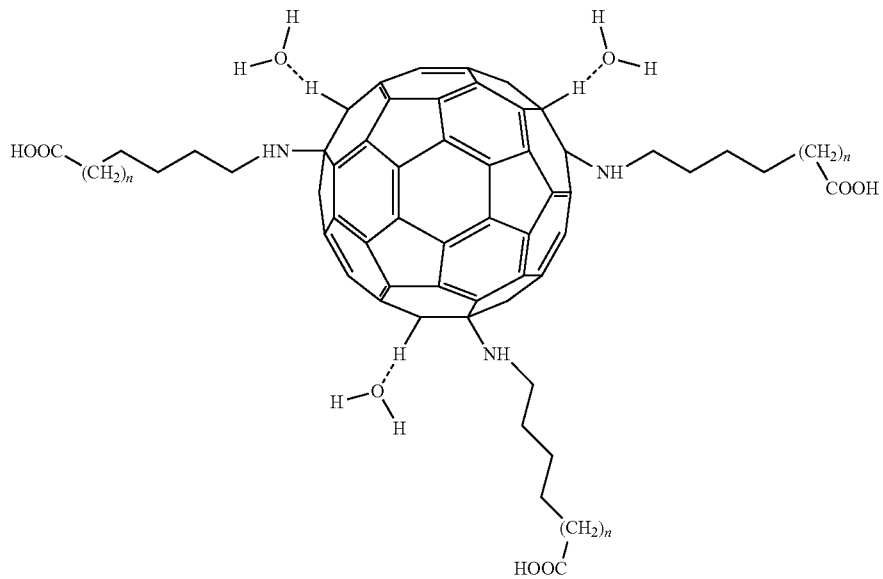

BACKGROUND ART

The utility of fullerenes as biologically active compounds has given an impetus to intensive development of the chemistry of functionalized derivatives of fullerenes, especially following the discovery of a high antiviral activity in some water-soluble fullerene (see Partha, R., and Conycrs, J. L. "Biomedical Applications of Functionalized Fullerene-Based Nanomaterials." Int. J. Nanomedicine, 2009 (4), 261-75; U.S. Pat. No. 6,204,391, 2005, "Water Soluble Fullerenes with Antiviral Activity;" R. Bakry et al., "Medicinal Application of Fullerenes," International Journal of Nanomedicine, 2007 (4), 639-649; and Z. Zhu, D. 1. Schuster, and M. Tuckermann, "Molecular Dynamics Study of the Connection between Flap Closing and Binding of Fullerene-Based Inhibitors of the HIV-1 Protease", Biochemistry, 2003, vol. 42, 1326-1333).

The medical use of fullerene derivatives is based on the lipophilic properties of the fullerene core, which enables fullerene derivatives to permeate cellular membranes, and the ability of fullerenes to generate in high quantum yield singlet oxygen, which splits DNAs. These properties endow functionalized fullerene derivatives with cytotoxic, antiviral, and other properties (see Bedrov, D., Smith, G. D., Davande, H., "Passive transport of fullerenes through a lipid membrane," J. Phys. Chem., B, 2008, Vol. 112., pp. 2078-84; Qiao, R., and Roberts A. E., "Translocation of Fullerene and Its Derivatives across a Lipid Bilayer", Nano Lett., 2007, Vol. 7, pp. 614-9; Nelsen, G. D., et al., "in vivo Biology and Toxicology of Fullerenes and their Derivatives", Basic and Clinical Pharrnnacology and Toxicology, 2008, Vol. 103, pp. 197-208).

Hydrated fullerene species have a high biological activity as bioantioxidants, which is due to the formation of active structural species of water clusters coordinated to the fullerene sphere (see Andrievsky, G. V., Brushkov, V. L, Tykhonov, A. A., and Gudkov S. V., "Peculiarities of the Antioxidant and Radioprotective Effects of Hydrated C60 Fullerene Nanostructures in vitro and in vivo." Free Radical Biology and Medicine, 2009, vol. 47, pp. 786-793).

The main problem hampering biological studies of fullerenes and their derivatives and the creation of medicaments on their basis arises from the difficulty of solubilizing fullerene systems in aqueous solutions.

A promising method for preparing water-soluble fullerene compositions is to chemically modify the fullerene sphere with hydrophilic solubilizing ligands.

Currently, a wide range of functionalized fullerenes have been prepared, wherein hydrophilic moieties are present in the side chains of ligands attached to the fullerene (the detergent type of complex), as well as spherical derivatives wherein polar groups are distributed over the fullerene sphere (this type includes fullerenols and amino adducts).

Amino acid derivatives of fullerenes have the greatest potential for use.

Non-native amino acids of the aliphatic raw containing six or more of methylene groups have some specific features in the context of hydration and biochemical activity. Spectroscopic studies of water structure in aqueous solutions of amino acids show that increasing the number of methylene groups spacing the amino group and the carboxy group enhances the destruction of water clusters. Pharmacological studies of derivatives of the extensive series of R—$(CH)_n$COOH amino acids showed a higher activity in systems where n is equal to or is higher than six.

Spherical amino acid derivatives of fullerene $C_{60}$ prepared by the reaction of nucleophilic addition of amino acids to the fullerene sphere at the amino group are described in Russian Federation patents Nos. 2196602, 2124022, and 2236852, and these patents can serve as the most pertinent pieces of prior art for our invention.

In the Russian Federation patent no. 2196602, there is claimed a method for inhibiting the reproduction of HIV and CMV infections by means of compounds based on amino acid and dipeptide fullerene derivatives. The amino acid fullerene derivatives used in that patent are sodium salts of fullerene aminocaproic acid and fullerene aminobutiric acid.

In the Russian Federation patent no. 2124022, in order to prepare fullerene aminocaproic acid, an aqueous solution of a potassium salt of aminocaproic acid and 18-crown-6 is added to a solution of fullerene in o-dichlorobenzene. The reaction mass is stirred for 6 to 8 hours at 60° C. Then, the solvents are distilled off, the residue is treated with a saturated potassium chloride solution, and the fullerene derivative residue is washed with water. The target product is obtained in quantitative yield. The resulting (monohydro)N-fullerene aminocaproic acid is soluble in dimethyl sulfoxide, dimethylformamide, and pyridine. The conditions for the final product to be separated are not defined in the synthesis method claimed in that patent.

The major drawback of the compounds prepared as described above, which are monoaddition products, consists in their water insolubility. One more drawback of the above-cited invention consists in that the phase-transfer catalyst used in the synthesis is crown ether, which is difficult to separate from the reaction products.

The Russian Federation patent no. 2236852 protects an agent for inhibiting the reproduction of enveloped viruses, this agent being fullerene polycarboxylic acid anions of general formula $C_{60}H_n[(CH_2)_mC(O)O^-]_n$ prepared by reacting the fullerene and an amino acid salt in an organic solvent medium in the presence of a poly(alkylene oxide).

In order to prepare those compounds, to a solution of fullerene in o-dichlorobenzene (or toluene, or another organic solvent), an amino acid is added as a salt (potassium or sodium salt) and then a solubilizing agent is added. The order in which the amino acid and solubilizing agent are added is unimportant; they can be added as a premixed complex. Useful solubilizing agents are various poly(alkylene oxides) (polyethylene glycols having molar weights from 150 to 400 or higher than 400 (for example, PEG-1500), as well as polyethylene glycols having free terminal groups, but also those with substituted terminal groups (for example, polyethylene glycol dimethyl ester having a molar weight of 500). In order to increase reaction rates, any strong reducing agent (an alkali metal) is added. The fullerene-to-amino acid ratio is increased by more than 50 times. Conversion to the desired pharmaceutically acceptable salt, especially to a sodium or potassium salt, is performed by treating the acid with a suitable base or by adding a salt of a weak volatile acid. In particular, a water-insoluble fullerene polycarboxylic acid is converted to a more preferable pharmaceutically acceptable, water soluble salt, for example to a sodium salt. Addition of a salt of a weak volatile acid is performed via treating the solution with an alkali metal salt of a weak volatile acid. Upon concentrating the solution by evaporation or freeze drying, the weak acid is removed and mixed fullerene polycarboxylic acids are recovered as mixtures of their alkali metal salts. The target product of that invention has a constant composition; the content of the major substance in the target product is as low as 87.8%.

The major drawbacks of the fullerene amino acid derivatives prepared by the method shown in the cited patent consist in that this method produces a mixture of fullerene carboxylate anions in the form of both salt and acid species. An individual compound cannot be prepared by the method described in the cited patent. Furthermore, the fullerene poly(amino acids) prepared by this prior-art method in the acid form are almost water insoluble. Attempts at preparing a stable pharmaceutical composition with fullerene polycarboxylic anions failed, because compounds are precipitating during storage. Fullerene poly(amino acids) influence leukopoiesis: they cause a shift of the leukocyte formula and induce the appearance of young forms of neutrophils (neutrophil metamyelocytes) in laboratory animals (rats and rabbits). In terms of safety (harmlessness), this indicates that these substances have toxicity which is responsible for the aforementioned alterations. The necessity of using in the synthesis of great excesses of a potassium or sodium salt of amino acids and great excesses of solvents gives rise to environmental problems in waste recycling, and increases the cost of the production process. For technological reasons alkali metals cannot be used to increase the reaction rate when chlorinated aromatic solvents are used.

DISCLOSURE OF THE INVENTION

The problem to be solved by the claimed technical solution consists in: the production of individual hydrated fullerene $C_{60}$ compounds with amino acids that would have antiviral activity against herpes virus, Hepatitis C virus, various influenza viruses, and HIV, and anti-tumor and anti-psoriatic activities and that would not cause a toxic effect on the body; a method to produce these compounds; and a pharmaceutical composition comprising these compounds.

In order to solve this problem, we propose a group of inventions that are linked to each other so as to form a single inventive concept, namely: a compound, a method for producing same, and pharmaceutical compositions comprising this compound pharmaceutical compositions.

The problem is solved by an individual hydrated compound of fullerene $C_{60}$ with amino carboxylic acids of general formula (II), where there are three covalently bonded amino acid moieties per fullerene molecule, these moieties comprising active hydration sites in their structures, thereby resulting in formation of water-soluble hydrates, and long hydrocarbon chains due to which water molecules can be retained in the inner coordination sphere of fullerene complexes.

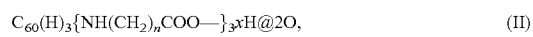

$$C_{60}(H)_3\{NH(CH_2)_nCOO—\}_3 \cdot xH@2O, \tag{II}$$

wherein $C_{60}$ is fullerene; n=5, 6, or 7; and x=8-10.

The problem is solved by the following means: hydrated amino acid fullerene derivatives of formula (II) are formed by reacting fullerene with a 15-fold molar excess of anhydrous potassium salts of amino acids in an aromatic solvent medium, comprising a slow addition to the resulting suspension of a phase-transfer catalyst under stirring and heating to a temperature not higher than 60-80° C. until the solution is completely decolorized and a solid residue is formed, this residue being then separated, followed by treating 0.8 M aqueous solutions of potassium salts of the fullerene amino acids with a 0.1 N solution of organic or mineral acids and men followed by centrifuging, washing, and drying the residue.

Further according to the invention, the anhydrous potassium amino acid salts are used in a finely dispersed state to enhance the reactivity of the process and the efficiency and profitability thereof, and the separation of the solid residue of potassium salts of fullerene amino acids is performed by filtering, ethanol washing, and drying. Useful phase-transfer catalysts are methyl esters of poly(ethylene oxides) having molecular weights of 200, 400, or 500, as most available and safe catalysts.

The problem is also solved by creating pharmaceutical compositions wherein the active agents are water-soluble hydrated fullerene amino acids of formula (II), which have antiviral activity against herpes virus, Hepatitis C virus, various influenza viruses, and HIV and have anti-tumor and anti-psoriatic activities.

The pharmaceutical compositions according to the claimed technical solution comprise a compound of general formula (II) in an amount that is efficient to attain the desired result, and can be administered as standard dosage forms (for example, as solid, semisolid, or liquid dosage forms), comprising a compound of the claimed technical solution as an active agent formulated with a carrier or an excipient suitable to be administered in the intramuscular, intravenous, oral, sublingual, inhalatory, topical, nasal, or rectal route. The active agent can be formulated in the composition together with ordinary nontoxic pharmaceutically acceptable carriers that are suitable for manufacturing solutions, tablets, pills, capsules, beads, suppositories, emulsions, suspensions, ointments, gels, and other dosage forms.

Particular drug administration levels and periodicity for a particular patient will depend on many factors, including the activity of a particular fullerene derivative, metabolic stability and length of action thereof; excretion rate; patient's age, body weight, general health, and gender; drug combinations; and the severity of the disease in the subject to be treated.

For oral administration in the form of suspensions, the compositions are prepared according to methods well known in the art of preparing pharmaceutical formulations, and they can comprise microcrystalline cellulose or derivatives thereof for providing the desired weight, alginic acid or sodium alginate as a suspending agent, methylcellulose as a viscosity enhancer, and sweetening agents and/or fragrances known in the art. When manufactured in the form of tablets, these compositions can comprise microcrystalline cellulose, calcium phosphate, starch, magnesium stearate, and lactose and/or other excipients, binding agents, expanders, disintegrants, diluents, and lubricants known in the art.

When intended to be administered as nasal aerosols or by inhalation, the compositions are prepared by methods well known in the art of pharmaceutical formulations, and they can be produced as solutions in physiological saline using benzoic acid or other suitable preservatives, adsorption promoters for enhancing bioapplicability, and/or other solubilizing or dispersing agents known in the art.

Solutions or suspensions for injections can be formulated according to known methods using nontoxic, parenterally applicable diluents or solvents, such as mannitol, 1,3-butanediol, water, Ringer's solution, or isotonic sodium chloride solutions; or suitable dispersing or wetting and suspending agents, such as sterile, soft, and stable oils, including synthetic mono- or diglycerides, or fatty acids, including oleic acid.

When intended for rectal administration in the form of suppositories, the compositions can be prepared by blending a drug with a non-irritating excipient, such as cocoa butter, synthetic glyceride esters, or polyethylene glycols, which are solid at ordinary temperatures but liquefy and/or dissolve in the rectal cavity to release the drug.

When administered topically in the form of ointments, gels, creams, liniments, etc., the compositions can be prepared by mixing active ingredients with an acceptable ointment base.

As an ointment base useful are grease, petroleum, or hydrophilic bases, such as petrolatum, mineral oil, paraffin, beeswax, lanolin, polyethylene glycol, and others.

As a basis for gels useful are methyl cellulose, sodium carboxymethyl cellulose, oxypropyl cellulose, polyethylene glycol or polyethylene oxide, carbopol, polyvinylpyrrolidone, polyvinyl alcohol, etc.

The invention relates to compounds, a method for producing these compounds, and pharmaceutically acceptable associations thereof with polar reagents. The compounds do not influence leukopoiesis: they neither cause a shift of the leukocyte formula, nor induce the appearance of young forms of neutrophils (neutrophil metamyelocytes) in laboratory animals (rats and rabbits). In terms of safety (harmlessness), this indicates that these substances have no toxicity which would be responsible for the aforementioned alterations. The claimed method produces different compositions comprising fullerene amino acids depending on the reagent ratio and process parameters, namely: water-soluble hydrated fullerene amino acids of general formula (II).

The method uses, at the synthesis step, optimal reagent ratios and minimal amounts of an organic solvent and a phase-transfer catalyst, followed by the recovery of claimed compounds using concentrated solutions of organic and mineral acids, thereby providing the quantitative production of tailored fullerene amino acid compositions and rendering the claimed method suitable for efficient and environmentally safe large-scale synthesis of these compositions.

The technical result of the claimed technical solution consists in the production of stable individual water-soluble hydrated fullerene $C_{60}$ compounds with aminocarboxylic acids that do not cause a toxic effect on the body. An efficient method has been developed to produce stable individual hydrated fullerene derivatives which have antiviral, antitumor, and anti-psoriatic activities.

The claimed invention will be illustrated by means of examples, which follow.

VARIANT EMBODIMENTS OF THE INVENTION

Example 1

Preparation of N-fullerene tris(δ-aminocaproic acid) hydrate (according to the IUPAC nomenclature rules: N-fullerene tris(6-aminohexanoic acid) hydrate) of formula $N—C_{60}(H_3)\{NH(CH_2)_5COOH\}_3 10H_2O$ To a solution of 60 g (0.08 mol) of fullerene $C_{60}$ in 4.5 L o-dichlorobenzene, added is 204 g (1.2 mol) of a finely divided anhydrous potassium salt of ε-aminocaproic acid. To the resulting suspension, added is for 2 hours under stirring and heating to a temperature not higher than 60° C., a mixture of o-dichlorobenzene and methyl polyethylene glycol 500 ether in the ratio 5:1. The reaction mixture is stirred at a temperature not higher than 60° C. for 5 hours until the solution completely decolorizes and a solid precipitate is formed. Following this, the mixture is filtered; the precipitate is washed on the filter with several ethanol portions and dried in vacuo a temperature not higher than 60° C. The isolated mixture of potassium salts of fullerene aminohexanoic acid is dissolved in 100 mL distilled water. To this solution, 0.1 N hydrochloric acid is added slowly under stirring until pH becomes 5.1. The mixture is allowed to stand until the product is completely precipitated. Then the aqueous layer is decanted. The residue, which is a fine suspension of the solid product in water, is centrifuged and washed with water to pH of 6. The residue is dried at a temperature not higher than 60° C. inside a vacuum drier.

The product is obtained in quantitative yield (115 g).

The compound is a dark brown solid which is soluble in water and in $CH_3CN:H_2O$ (1:10) and $DMF-H_2O$ (1:100).

Thermogravimetric analysis shows that the compound contains 10 $H_2O$ moles. At 350° C., an intense destruction of the complex occurs. The decomposition residue contains fullerene and oxidation products thereof.

The IR spectrum of product (I) features absorption bands characteristic of N-substituted amino acids: for —COOH— group, at 1704 $cm^{-1}$ and 1658 $cm^{-1}$; for N—H— stretching vibrations, at 3400 $cm^{-1}$; for N—H bending vibrations, at 1552 $cm^{-1}$; and for $C_{60}$—NH—R—, absorption bands appear at 1104 $cm^{-1}$, 930 $cm^{-1}$, and 830 $cm^{-1}$.

The electronic absorbance spectrum of the product does not feature absorption bands from free fullerene.

Elemental analysis shows the following element ratios: % C=72.75; % H=4.70; % N=2.32; for the bulk formula $C_{78}H_{39}O_6N_3 10H_2O$ calcd.: % C=72.38, % H=4.3, % N=3.24.

The number of carboxy groups in the product is derived from reactions with metal salts and amines. In reaction with silver nitrate the complex of composition $C60(H)_3\{NH(CH_2)_5COOAg\}_3 10H_2O$ was isolated quantitatively (found: % Ag=20.88, % C=57.80, % N=2.51, % H=3.32; for $C_{78}H_{36}O_6N_3Ag_3(10H_2O)$ calcd.: % Ag=20.00, % C=57.88, % N=2.60, % H=3.46).

Reaction with trisamine yielded a water-soluble complex of composition $C60(H)_3\{NH(CH_2)_nCOO^-NH_3^{+}C(CH_2OH)_3\}_3$ (found: % C=64.88, % H=4.56, % N=5.08, for $C_{90}H_{72}O_{15}N_6 10H_2O$ calcd.: % C=65.2, % H=4.34, % N=5.10).

Example 2

Preparation of N-fullerene tris-ω-aminoenanthic acid) hydrate (according to the IUPAC nomenclature rules: N-fullerene-(tris-7-aminoheptanoic acid)hydrate) of formula N—$C_{90}(H_3)\{NH(CH_2)_6COOH\}_3 8H_2O$ To a solution of 72 g (0.1 mol) of fullerene $C_{60}$ in 4 L o-dichlorobenzene, added is 182 g (1.2 mol) of finely divided anhydrous potassium salt of ω-aminoenanthic acid. To the resulting suspension, added is for 3 h under stirring and heating to a temperature not higher than 80° C. a mixture of o-dichlorobenzene and methyl polyethyleneglycol 500 ether in the ratio 5:1. The reaction mixture is stirred at a temperature not higher than 80° C. for 8 h until the solution is completely decolorized and a solid precipitate is formed. Following this, the mixture is filtered; the precipitate is washed on the filter with several ethanol portions and dried in vacuo at a temperature not higher than 60° C. The isolated mixture of potassium salts of fullerene aminoenanthic and aminoenanthic acids is dissolved in 120 mL distilled water. To this solution, 0.1 N hydrochloric acid is added slowly under stirring until pH becomes 5.1. The mixture is allowed to stand until the product is precipitated completely. Then, the aqueous layer is decanted. The residue, which is a fine suspension of the solid product in water, is centrifuged and washed with water to pH of 6. The residue is dried at a temperature not higher than 60° C. inside a vacuum drier.

The product is obtained in quantitative yield (130 g).

The compound is a dark brown solid which is soluble in water and soluble in $CH_3CN:H_2O$ (1:10) and $DMF-H_2O$ (1:100).

Thermogravimetric analysis shows that the compound contains 8 $H_2O$ moles. At 450° C., the complex experiences intense destruction. The decomposition residue contains fullerene and oxidation products thereof.

The IR spectrum of the product features absorption bands characteristic of N-substituted amino acids: for —COOH— group, at 1707 $cm^{-1}$ and 1650 $cm^{-1}$; for N—H stretching vibrations, at 3400 $cm^{-1}$; for N—H bending vibrations, at 1552 $cm^{-1}$; and for $C_{60}$—NH—R—, absorption bands appear at 1104 $cm^{-1}$, 930 $cm^{-1}$, and 830 $cm^{-1}$.

The electronic absorbance spectrum features an absorption band at 260 nm.

Elemental analysis shows the following element ratios: % C=72.75; % H=4.70; % N=2.32; for the bulk formula: % C=73.55; % H=4.60; % N=3.18; for the bulk formula $C_{81}H_{45}O_6N_3$ ($8H_2O$) calcd.: % C=74.82, % H=4.69, % N=3.23.

Reaction with silver nitrate yielded a silver salt of fullerene amino acid, which quantitatively proves the occurrence of three amino acid moieties in the product.

Example 3

Preparation of N-fullerene tris(8-aminooctanoic acid hydrate) of formula N—$C_{60}(H_3)\{NH(CH_2)_7COOH\}_3 10H_2O$ The protocol is as in Example 1, with the only difference that a potassium salt of aminooctanoic acid is used instead of finely divided anhydrous potassium salt of ε-aminocaproic acid (ω-aminoenanthic acid). The analysis of the resulting compound proves the above composition of the complex.

The antiviral activity of the compound was studied against HIV, HSV, and influenza virus; its antitumor activity was also studied. The compound has high antitumor and antiviral activities against all of the aforementioned viruses. Preferred example embodiments of the invention are given below. In the examples that follow, the compound prepared by the method described in Example 1 will be referred in the text as agent 1 (fullerene tris(aminocaproic acid) hydrate).

Example 4

Anti-HIV Activity of Fullerene Tris(Aminocaproic Acid)

These studies were carried out at the Ivanovsky Research Institute for Virology, Russian Academy of Medical Sciences, Moscow. The task was to study the anti-HIV activity of the agent.

Cells were added with the test agent and infected with the virus in a dose of 0.01 $TCD_{50}$/cell. Cell cultures were incubated at 37° C. under a 5% $CO_2$ atmosphere and 98% humidity for 4 to 5 days. The results were ascertained by staining the cells with a dye and by optical microscopy: studies of the cytopathic effect (CPE) of the virus and virus-induced syncytium formation (syncytium is a conglomerate of several cells having an all-enclosing cell membrane formed through membrane fusion).

The degree of cytodestruction was assessed under the microscope according to the commonly accepted four-plus system using "+" and "−" symbols according to the number of dead cells in each of the four wells corresponding to one test parameter.

++++ means the 100% death of cells in the four wells used in a single-dilution test;
+++ means the 75% death of cells in the four wells;
++ means the 50% death of cells in each of the four wells;
+ means the 25% death of cells in each of the four wells;
+− means the onset degeneration; and
− means the absence of cytodestruction.

The results of these studies are displayed in Tables 1 and 2.

These results (see Tables 1 and 2) show that agent 1 has an antiviral activity against the type 1 human immunodeficiency virus in concentrations of 1 to 10 mcg/mL. The $EC_{50}$ (50% effective concentration) of the agent is 5.0 mcg/mL.

Example 5

Antiviral Activity of Fullerene Tris(Aminocaproic Acid) Against the Influenza Virus These studies were performed at the Ivanovsky Research Institute for Virology, Russian Academy of Medical Sciences, Moscow. The task was to study the antiviral activity of the agent in MDCK cell culture against the A/IIV-Moscow/01/2009 (H1N1)swl influenza virus.

The agent was diluted with DMSO (5 mg substance +0.5 mL DMSO), followed by addition of 4.5 mL of the MEM cell cultural medium to obtain in this way a stock solution with a concentration of 1.0 mg/mL. Subsequently, the stocks were diluted with the MEM medium to obtain the following series of working concentrations: 6.5 mcg/mL-12.5-25.0-50.0-100 mcg/mL.

The antiviral activity was ascertained from the reduction of influenza virus reproduction in the MDCK cell culture, as recognized by ELISA.

For this purpose, MDCK cells were grown on 96-well plates to obtain a complete monolayer, washed from the growth medium, and added with substances in a twofold concentration in 100 mcL MEM medium. Infection with the virus in a working dose ranging from 100 to 1000 $TCD_{50}$ was carried out following two protocols: 2 hours following the injection of the substances and simultaneously. The plates were incubated in a thermostat filled with $CO_2$ for 24 hours at 37° C. Following the incubation, the medium was removed and cells were fixed by 80% acetone in PBS for 15 minutes and then well dried, and ELISA was performed by consecutive adsorption of specific reagents, namely, monoclonal antibodies, conjugate, and substrate (orthophenylenediamine). The degree of reaction was monitored by measuring optical density at 492 nM on a Biokom spectrophotometer. Each virus dilution was studied in three replicas, for which an average optical density (OD) value was calculated. Percent inhibition was determined as the quotient of the difference between the experimental OD and the OD of the cell control, divided by the difference between the OD of the virus control and the OD of the cell control, multiplied by 100%. The data gained in this way were used to determine the minimal concentration of the agent causing the 50.0% inhibition of viral reproduction ($MIC_{50}$).

The inhibition of A(H1N1) influenza virus reproduction was ascertained in three experiments with different multiplicities of infection. The results are displayed in Table 3 (as protocols of the three experiments) and in Table 4 (as average results of the three experiments).

One can see from Table 4 that the series of agent 1 shows the highest activity in reduction of influenza virus reproduction in the MDCK cell culture. There is a clear-cut correlation between the degree of reproduction and the concentration of the agent: as the concentration increases, virus reproduction decreases. Further, there is no noticeable difference in values regardless of the infection protocol (2 hours post injection of the agent or simultaneously). The minimal concentration of the agent causing the 50.0% inhibition of viral reproduction ($MIC_{50}$) was 9.5 mcg/mL in the protocol where the agent was injected 2 hours prior to infection and 12.5 mcg/mL for the simultaneous injection. The calculations were performed by graphical data processing.

Thus, the activity values obtained for different series of agent 1 against the A/IIV-Moscow/01/2009 (H1N1)swl influenza virus demonstrate a high reproduction inhibitory activity in the MDCK cell culture for series 1, with a moderate activity found for series 2. The agent administration protocol (2 h prior to infection or simultaneously with infecting) does not affect the activity of the agent in the MDCK cell culture.

Example 6

Antiviral Activity Studies of Fullerene Tris(Aminicaproic Acid) on Induced Influenza Pneumonia in Mice These studies were performed at the Medicinal Chemistry Center (TsKhLS-VNIKhFI), Moscow.

The agent 1 used in these studies was a dark brown powder. The doses of the agent required for oral administration were prepared by dissolving weighed portions thereof in a 1% starch solution cooked with water. For intraperitoneal or intramuscular administration, weighed portions of agent 1 were dissolved in 1.5% dimethyl sulfoxide solution.

The virus used was mouse-adopted A/Aichi/2/69 (H3N2) influenza virus. This virus is widely used to determine the efficiency of antiviral agents in induced influenza pneumonia in mice and was purchased from the Museum of Viral Strains and Cell Cultures of the Ivanovsky Research Institute for Virology, Russian Academy of Medical Sciences. In order to prepare the infecting material, mice were infected intranasally with the allantoic virus; once symptoms of the disease developed, the mice were killed and a lung tissue homogenate was prepared under sterile conditions. Then, this homogenate was used to infect 10-day chicken embryos, from which the allantoic virus was derived to be used, after titrating it in mice, to infect animals.

Non-pedigree (female) white mice having body weights of 12 to 14 g were purchased from the Andreevka nursery (Moscow oblast) and maintained on a standard ration in regulated vivarium conditions.

Pre-weighed mice (nonlinear female mice with average body weights of 12 to 14 g) were infected intranasally under light ether anesthesia with the A/Aichi/2/69 (H3N2) influenza virus ($10LD_{50}$ in 100 mcL). The $LD_{50}$ was determined in a preliminary experiment by titrating the allantoic virus in mice that were like those then used in the major experiment. The treatment scheme with the test agent was as follows: 24 hours prior to infection, 1 hours prior to infection, 24 hours post infection, and then once a day in 24 hours for 5 days. For oral administration, an insulin syringe with a special needle (lavage) was used; each dose was administered in an amount of 100 mcL. For intraperitoneal and intramuscular administrations, each dose was also injected in an amount of 100 mcL. The virus control group was comprised of 10 mice that were infected with the virus but not treated by agents. In the experiment there were also two groups of uninfected mice each, each mouse injected intraperitoneally and intramuscularly with 100 mcL of 1.5% DMSO, which was used as the solvent for agents. The other groups were also each initially comprised of 10 animals. The treated and control animals were monitored daily; in the first five days post infection, the mice were weighed every day, and then every next day. The chemotherapeutic activity of agent 1 in induced influenza pneumonia was ascertained by three criteria, namely: index of protection from lethal viral infection, an increase in average lifetime, and a decrease in body weight loss in the groups of animals treated with the agent, compared to the control group.

Treatment with agent 1 was efficient in decreasing the death rate from influenza pneumonia in mice and weight loss thereof, and increasing the average lifetime compared to the virus control. The efficiency of this treatment depended on the dose of the agent and the treatment scheme. The efficiency of oral treatment with fullerene tris(aminocaproic acid) hydrate increased as the dose of the agent increased. Oral treatment with agent 1 was efficient, increasing the average lifetime by a factor of 1.6 to 1.7. Intramuscular treatment with fullerene tris(aminocaproic acid) hydrate was most efficient in terms of all of the three parameters (index of protection from death, average lifetime, and weight loss); when administered in doses of 100 and 200 mg/kg/day, this treatment prevented the death of 70 to 80% of the infected animals and weight loss in them, and also increased their lifetime almost twofold.

Intraperitoneal treatment with fullerene tris(aminocaproic acid) was efficient only in doses of 50 and 100) mg/kg/day. The death rate, a considerable reduction in average lifetime and in body weight in mice upon intraperitoneal treatment thereof with agent 1 in a dose of 200 mg/kg/day imply that this dose with this administration method is toxic for the infected mice. The results are displayed in Tables 5 and 6.

Example 7

The Protective Activity Studies of Fullerene Tris(Aminocaproic Acid) in Experimental Lethal Influenza Infection in White Mice Caused by Viruses of Various Origins These studies were performed at the Research Institute for Influenza, St. Petersburg.

The agent 1 used in the studies was a black finely divided powder. Weighed samples of the agent were dissolved in the Igla MEM cell culture medium (BioloT, St. Petersburg, cat. 20 No. 1.3.3). The resulting solution was used to prepare dilution series in the MEM medium in order to determine the antiviral activities of samples in animal experiments.

As reference agents used were Remantadine (1-(1-adamantyl)-aminoethyl hydrochloride. Aldrich Chem. Co., 25 Milw., Wis., cat. No. 39.059-3) and Tamiflu (ethyl(3R,4R, 5S)-4-acetamido-5-amino-3-(1-ethylpropoxy)-1-cyclohexene-1-carboxylate phosphate, Hoffmann LaRoche, Switzerland).

Viruses. The viruses used in the study were mouse-adopted influenza viruses of the following strains:
A/Swine/1976/31 (H1N1) (porcine derived);
A/Puerto Rico/8/34 (H1N1) (human-derived and Remantadine-resistant); and
A/Vladivostok/2/09 (H1N1) (human-derived and Tamiflu-resistant).

The viruses were passaged in the allantoic cavities of 10- to 12-day chicken embryos for 48 hours at 36° C. The A/Vladivostok/2/09 (H1N1) strain was pre-adopted to mice by means of three alternating passages in animals and in chicken embryos.

A virus-containing allantoic fluid of chick embryos was used to infect animals. It was used to prepare a series of 10-fold dilutions in physiological saline, after which the infectivity of the virus in the infecting material was determined in a separate experiment by titrating animals for lethality. The virus titer was calculated by the Reed-Muench method (see Am. J. Hyg., 1938, 27:493-497).

Non-pedigree white mice (females) having body weights of 14 to 16 g were purchased from the Rappolovo nursery (Leningrad oblast) and maintained on a standard ration in regulated vivarium conditions at the Research Institute for Influenza, the Russian Academy of Medical Sciences. Selection of animals in experimental groups was conducted by random sampling. Before tests the animals were under observation for two weeks.

Tested agents were administered to animals intraperitoneally in an amount of 0.2 mL in the following doses: for agent 1: 300, 100, and 30 mg/kg; for Remantadine: 50 mg/kg; and for Tamiflu: 20 mg/kg animal body weight. The agents were administered in a treatment-preventive scheme, as follows: 24 hours and 1 hour prior to infection and 24, 48, 72 hours post infection. The placebo control group was injected with saline phosphate buffer. The negative control was intact animals that were kept in the same conditions as the experimental groups.

Viruses were administered to the animals intranasally under light ether anesthesia at a dose 1 and 10 $LD_{50}$. Twenty five mice were taken for each observation group. On day 5 post infection, 10 animals from each group were euthanized and autopsied, and lungs were isolated. Of these 10 lungs, five were used to isolate the virus (they were frozen and stored at −20° C. until relevant experiments were carried out); the other five were fixed with formalin and then used in histological analysis (see below).

The other animals were monitored for 14 days, that is, for a period of time during which the death rate of animals is detected in induced influenza. The animal death rates in the control and experimental groups were recorded daily. The death rates obtained in this way were used to calculate percent mortalities (M: the ratio of the animals that died in 14 days to the overall number of infected animals in a group), index of protection (IP: the ratio of the percent mortalities in the control group and experimental groups to the percent mortality in the control group), and average lifetime of animals (DL) at the rate of 14 days of observation.

Animals that survived to day 15 after infection were autopsied, and the area of post-influenza pneumonia lesions in lungs was visually evaluated. The lesion size was expressed as percent of the total surface of the lungs.

Clinical signs of the disease were typical of influenza infection and included the shortness of breath, ataxia, tremor, a reduction in feed intake and water, and as a consequence, a reduction in body weight.

Data on the death rate dynamics in animals in the control and experimental groups are summarized in Tables 7 to 9.

As can be seen from these results, the influenza virus caused lethal infection in white mice, accompanied by the death of animals starting from days 3-4 after infection, depending on the dose of virus. The lifetime of animals related to the dose of virus inversely. Remantadine, which was used in the experiment as the reference agent, had a very moderate protective effect against this infection, manifested as some reduction in death rate in the experimental groups compared to the control (the index of protection was 13 to 29%) and as an insignificant increase in lifetime (by 1.1 to 1.6 days depending on the dose of virus). Thus, these data agree with earlier results of in vitro and in vive experiments, which proved that the virus strain used was insensitive to Remantadine. The moderate protective effect observed in this case may be explained as arising from the antitoxic effect of the agent.

At the same time Tamiflu (the reference agent) showed a well-defined protective effect, both reducing the death rate in the groups of mice that received treatment (by approximately 70% compared to the control), and increasing the average lifetime of animals (by 2 to 6 days). Thus, the virus used was resistant to Remantadine, but sensitive to Tamiflu.

In data analyzing it was found that the test sample of the agent in the protective properties thereof approached the Tamiflu reference agent (fable 7).

These results were confirmed using induced influenza pneumonia caused by the other two strains of the influenza virus. Data from these experiments are summarized in Tables 8 and 9.

As can be seen from these data, the activity of chemotherapeutic agents against the viruses used was greatly differentiated. For example, the etiotropic agent Tamiflu was inactive against the A/Vladivostok/2/09 influenza virus strain. Thus, the earlier gained data that this isolate is resistant to Tamiflu were confirmed in animal experiments. At the same time, the activity of the test agent against this strain was very high, and this is undoubtedly to be regarded as an advantage of the agent.

The activity index of the test agent (the index of protection, namely, lifetime extension) was 21 to 72% and 0.8 to 4.4 days, depending on the strain used, the infecting dose of virus, and the dose of the agent.

For studying the effect of agent 1 on the replicative activity of influenza viruses in the lung tissue of infected animals, on day 3 post infection homogenizates were prepared from the lungs of animals to be then used to determine the infective titer of the virus in the cell culture. Replication level values for model influenza viruses in animal's body are displayed in Table 10.

As can be inferred from these results, all the three of viruses used were able to replicate efficiently in the lungs of mice, reaching by day 3 titers of 3.4 to 6.4 $\log_{10} EID_{50}/20$ mg depending on the strain used and the infecting dose of virus. The chemotherapeutic agents used, namely the tested agent and reference agent, limited the multiplication of the virus to different degrees. For example, Remantadine insignificantly (by two to three orders of magnitude) reduced the infectiveness of A/Swine/1976/3 and A/Vladivostok/2/09 sensitive viruses, but did not show reliable inhibitory activity against the Remantadine-resistant strain A/Puerto Rico/8/34. Tamiflu was active against A/Swine/1976/31 and A/Puerto Rico/8/34 viruses. At the same time, when Tamiflu was tested in model resistant strain A/Vladivostok/2/09, some reduction in infectious virus titers was found; differences from the control were, however, insignificant.

The tested agent showed a substantial inhibitory activity against all of the viruses studied. The activity level did not exceed but was commensurate to the activities of the reference agents (Remantadine and Tamiflu). As regards the activity against viruses that are resistant to chemotherapeutical agents, the test agent had a far higher activity, than Tamiflu, against Oseltamivir-resistant strain A/Vladivostok/2/09 and a higher activity, than Remantadine, against Remantadine-resistant strain A/PR/8/34.

In studying the morphogenesis features of experimental influenza infection with treatment-preventive administration of agent 1 at a dose of 300 mg/kg, it was noticed that the morphogenesis of the infection process in the lungs of animals that received the agent was very different from the morphological changes in the lungs of control animals. The main difference observed on day 3 post infection consisted in the nature of the inflammatory exudate, namely that with the same intensity thereof, cells in the stage of decay were almost not observed, these cells being specific to the acute phase of influenza pneumonia. The cellular component of the exudate was represented exclusively by intact neutrophils, lymphocytes and macrophages. In a cation, tle serous and hemorrhagic components of the exudate were also less pronounced. Bronchial epithelial cells appeared more intact than in the control animals. The inflammation sites themselves occupied a smaller area than in the control animals.

The same trends were observed in post-influenza pneumonia. Lesion sites in the lungs were considerably confined in size; morphological studies showed moderate epithelial metaplasia and interstitial infiltration with intact neutrophils and round cell elements. It should be mentioned that the effect of the agent was observed when animals were infected with any of the three studied viruses, regardless of their sensitivity or resistance to reference agents.

An additional criterion for the protective effect of agent 1 was the size of sites of chronic lung lesions in animals. The results of this test are displayed in Table 11.

As seen from the results, all of the three viruses induced the formation of persistent chronic lesions in the lungs which were detected visually in the surviving animals on day 15 after infection. The reference agents (Remantadine and Tamiflu) reliably reduced the extent of post-influenza pneumonia lesions caused by viruses that were sensitive to these agents, and were inactive against resistant strains. At the same time, agent 1 reliably reduced this value regardless of the virus used.

Thus, in the concentrations studied (300 to 30 mg/kg), agent 1 was shown to have a dose-dependent protective activity in the models used. This activity was manifested in the following values:
  6- to 200-fold reduction in infectious virus titers in the lung tissue of infected animals;
  extension of the lifetime of infected animals (by 0.1 to 4.4 days depending on the strain, virus dose, synthesis batch, and agent dose);
  reduction in specific mortality in experimental groups by 7 to 72% depending on the strain, virus dose, synthesis batch, and agent dose; and
  2- to 4-fold reduction in average extent of chronic post-influenza pneumonia lesions.

In the combination of these values, the protective activity of agent 1 at some doses is commensurate to the activity of the Remantadine reference agent.

These data show that agent 1 has a high anti-influenza activity, specifically against strains of swine origin, and against viruses that are resistant to Remantadine and Tamiflu anti-influenza agents used in clinical practice.

Example 8

Antitumor Activity Studies of Fullerene Tris(Aminocaproic Acid) on Induced Solid and Ascites Ehrlich Carcinoma in White Mice The tasks of these studies were as follows:
to study the effect of agent 1 on the ascites tumor growth dynamics with intraperitoneal administration of cancer cells;

to study the effect of agent 1 on the solid tumor growth dynamics and to study the effect of agents on the morphology and morphometric characteristics of solid Ehrlich carcinoma; and to study the effect of agent 1 on the apoptotic activity of Ehrlich ascites carcinoma cells.

An aqueous solution of agent 1 was used in the study at two doses: in concentrations of 30 and 10 mg/kg. Animals were each injected subcutaneously with 0.2 mL of the solution of each concentration 24 hours prior to inoculation and then daily during the entire time of the experiment. The final concentrations of the agent were 300 and 100 mg/kg body weight.

The reference agent used was Cisplatin (an antitumor agent used in the practice of human cancer therapy). Cisplatin was administered once on day 2 post tumor implantation because of its high toxicity. The final Cisplatin concentration was 5 mg/kg body weight.

The experiments were carried out on non-pedigree white mice having average body weights of 20±3 g (purchased from the Rappolovo animal farm, Leningrad oblast).

Ehrlich carcinoma cells were purchased from the Museum of Cellular Lines of the Research Institute for Oncology and cultured in the peritoneal cavities of white mice. For this purpose, 0.2 mL, cell suspension was administered to animals intraperitoneally. In 7 to 10 days post inoculation, the animals were killed; the ascitic fluid was collected through an abdominal puncture, diluted 10-fold with saline, and placed on ice.

In order to induce the solid Ehrlich carcinoma, 0.2 mL cell suspension was injected to each animal subcutaneously in the region of the right hip within 40 minutes following the collection of the ascitic fluid placed on ice animals. In the course of experiment, tumor nodules were measured with a micrometer during 28 days twice a week starting on day 8 post inoculation. The tumor size was calculated by multiplying half the length of the nodule by the squared width and expressed in cubic millimeters. The death rate of animals was scored in control and experimental groups. The animals were euthanized on day 29 post transplantation.

To study the effect of agents on ascites tumor, animals were injected intraperitoneally with 0.2 ml of cell suspension within at most 40 minutes after the collection of the initial ascitic fluid. The body weights of mice were monitored during the experiment to be an indicator of ascitic fluid accumulation in the peritoneal cavity. The animals were observed for 16 days. On day 17 post transplantation, the animals were euthanized.

The dynamics of tumor growth and mortality rates in animals with ascites carcinoma in the control group and experimental groups are displayed in Table 12.

As seen from the results, the inoculation of tumor cells into the peritoneal cavity of animals caused a rapid accumulation of ascitic fluid inside the cavity. The use of therapeutic agents had a pronounced therapeutic effect and led to inhibition of ascites accumulation.

The treatment of animals with the claimed agent and the reference agent (Cisplatin) has led to a significant slowdown of the dynamics of body weight gain in animals. In the later stages of the process, these differences reached statistical significance.

The effect of the agent on apoptosis processes in ascites Ehrlich carcinoma cells of moderate size and granularity in white mice is seen in Tables 13 and 14.

As follows from the results, only a small fraction of tumor cells in both tumor subpopulations was in a stage of reversible or irreversible apoptosis in the control animals. The use of Cisplatin caused a strong rise in the fraction of cells in an early apoptosis stage among the immune cells (Table 13) and late apoptosis and necrosis among the tumor cells (Table 14).

Agent 1 acted at the level of Cisplatin: as the reference agent, it promoted early apoptosis in immune cells and late apoptosis in the tumor cell subpopulation. The agent almost did not leave live ($AnV^-/AAD^-$) tumor cells. As regards the necrosis induction level in tumor cells, the agent even surpassed Cisplatin (30.2% against 26.6% for Cisplatin). The mechanism of the antitumor effect of agent 1, as that for Cisplatin, consisted in inducing apoptotic processes in tumor and immune cells that constitute ascites. The apoptosis process went selectively and reliably more rapidly in tumor cells than in neutrophils and lymphocytes that are in the ascitic fluid.

The results of cytofluorimetric analysis imply a selective effect of the reference agent (Cisplatin) on the tumor cells compared to normal white blood cells, also present in the ascitic fluid. At the same time after the administration of the agent, normal cells that constitute the fraction of moderate size and granularity (neutrophils, macrophages, lymphocytes and other) were in the early apoptosis phase while tumor cells were in the late (irreversible) apoptosis or necrosis phase.

Data on the dynamics of development of a solid tumor under the agent and Cisplatin compared to the control group of animals are displayed in Table 15.

As seen from the results, all of the agents used to some extent inhibited tumor growth throughout the experiment. In general, Cisplatin had the most pronounced antitumor activity. When it was administered, reliable inhibition of tumor growth was noted until day 17 after transplantation.

At the same time, both series of the agent also showed a dose-dependent antitumor effect. Reliable reduction in tumor size and inhibition of its growth were noted until day 8 of the experiment. Later, agents also checked the growth of the tumor at all stages of the study, although the differences with the control did not reach statistical reliability. On the whole, Agent 1 at a dose of 100 mg/kg body weight may be noticed as the closest to Cisplatin almost at all stages of the experiment.

The results do not allow us to consider agent 1 as a leading agent for targeted therapy of cancer diseases. However, based on these data, we can talk about it as a promising tool for further development of a complex therapeutic agent to be used together with other antitumor agents, especially in ascites tumors.

Pharmaceutical dosage forms of the claimed agent can be administered orally, parenterally (including subcutaneous injections; intravenous, intramuscular, or gluteal injection and infusion), by inhalatory spraying or rectally for the treatment or prevention of viral infections such as HIV, herpes, and various influenzas, as well as antitumor agents for use in complex therapy.

Compounds are mixed with conventional pharmaceutical carriers and excipients and are used in the form of tablets, capsules, suppositories, ointments, emulsions, solutions, or sprays. It should be noted that in order for solutions, sprays, and soft dosage forms (ointments, suppositories) to be prepared, the compounds are pre-diluted in a mixture of DMSO and water.

The treatment of infectious diseases by pharmaceutically acceptable doses of compounds of formula (II) simultaneously affects more than one virus (in the case of mixed infections) and addresses the different stages of virus replication. The treatment was shown to be accompanied by a reduction of the stress response to the administration of the agent, an enhancement of the antioxidant protection of the body from infections, and removal of toxins. Intoxication is characteristic of a number of viral infections and is responsible for the disease severity.

Compounds of formula (II) can be combined with other antiviral agents, immunomodulating agents, anti-infection agents, or vaccines in various combinations with any pharmaceutical formulations intended for treatment.

TABLE 1

Cytotoxicity of the claimed agent studied in human lymphoblastoid cells model

| Run parameters, concentration, mcg/mL | | Cell survival rate, % | Number of cells × $10^3$/mL |
|---|---|---|---|
| Cell control | | 96 | 833 |
| Agent 1 | 0.5 | 95 | 633 |
| | 1.0 | 94 | 599 |
| | 5.0 | 96 | 530 |
| | 10.0 | 92 | 500 |
| | 100 | 70 | 433 |

TABLE 2

Antiviral activity of agent 1 studied on HIV-1 infected human cell model

| Run parameters | Concentration, mcg/mL | Cell survival rate, % | Number of cells × $10^3$/mL | CPE/syncytia (+) |
|---|---|---|---|---|
| Cell control | 0 | 96 | 83.3 | 0 |
| Virus control | 0 | 20 | 83.5 | 4.0 |
| Agent 1 | 0.5 | 27 | 133.2 | 4.0 |
| | 1.0 | 75 | 320.4 | 2.0 |
| | 5.0 | 92 | 480.0 | 0 |
| | 10 | 95 | 579.3 | 0 |

TABLE 3

Activity values of agent 1 against influenza virus A/IIV-Moscow/01/2009 (H1N1)swl

| Concentration of the agent (mcg/mL) | Administration protocol | Percent (%) reduction of influenza virus reproduction in MDCK cell culture relative to control in the presence of series of the claimed agent |
|---|---|---|
| 6.25 | 2 h prior to infection simultaneously with infection | 24.0-80.0-0 54.0-21.0 |
| 12.5 | 2 h prior to infection simultaneously with infection | 45.0-100-6.0 78.0-37.0 |
| 25.0 | 2 h prior to infection simultaneously with infection | 40.0-100-43.0 88.0-35.0 |
| 50.0 | 2 h prior to infection simultaneously with infection | 47.0-77.0-69.0 96.0-43.0 |
| 100.0 | 2 h prior to infection simultaneously with infection | 72.0-88.0-66.0 69.0-76.0 |

TABLE 4

Activity values of agent 1 against influenza virus A/IIV-Moscow/01/2009 (H1N1)swl, average values

| Concentration of the agent (mcg/mL) | Administration protocol | Percent (%) reduction of influenza virus reproduction in MDCK cell culture relative to control in the presence of series of the claimed agent |
|---|---|---|
| 6.25 | 2 h prior to infection simultaneously with infection | 35.0 38.0 |
| 12.5 | 2 h prior to infection simultaneously with infection | 50.0 58.0 |
| 25.0 | 2 h prior to infection simultaneously with infection | 61.0 62.0 |
| 50.0 | 2 h prior to infection simultaneously with infection | 64.0 70.0 |
| 100.0 | 2 h prior to infection simultaneously with infection | 75.0 73 |

TABLE 5

Efficiency of fullerene tris(aminocaproic acid) hydrate in influenza infection induced in mice

| | On observation day 16 | | | |
|---|---|---|---|---|
| Dose of the agent | Survival (survivors/total) | Death rate (%) | Percent death protection (%) | Average lifetime (days)** |
| Fullerene tris(aminocaproic acid) hydrate orally | | | | |
| 100 mg/kg/day | 5/10 | 50 | 40 | 10.4 (2-7 d., 1-9 d., 1-10 d) |
| 200 mg/kg/day | 7/10 | 30 | 60 | 13.0 (1-7 d., 1-10 d., 1-11 d) |
| Fullerene tris(aminocaproic acid) hydrate intramuscularly | | | | |
| 50 mg/kg/day | 6/10 | 40 | 50 | 12.4 (1-7 d., 1-9 d., 2-11 d) |
| 100 mg/kg/day | 8/10 | 20 | 70 | 13.5 (1-8 d, 1-9 d) |
| 200 mg/kg/day | 9/10 | 10 | 80 | 14.4 (1-10 d) |
| 1.5% DMSO solution | 10/10 | 0 | | >16 |
| Fullerene tris(aminocaproic acid) hydrate intraperitoneally | | | | |
| 50 mg/kg/day | 5/10 | 50 | 40 | 11.5 (1-5 d., 1-7 d., 3-11 d.) |
| 100 mg/kg/day | 5/10 | 50 | 40 | 11.0 (3-7 d., 1-8 d., 1-11 d) |

TABLE 5-continued

Efficiency of fullerene tris(aminocaproic acid) hydrate in influenza infection induced in mice

| | On observation day 16 | | | |
|---|---|---|---|---|
| Dose of the agent | Survival (survivors/total) | Death rate (%) | Percent death protection (%) | Average lifetime (days)** |
| 1.5% DMSO solution | 10/10 | 0 | | >16 |
| Virus Control (10LD$_{50}$) | 1/10 | 90 | | 7.3 (5-7 d., 4-8 d.) |

*Treatment scheme: 24 hours and 1 hour prior to infection, then in 24, 48, 72, and 96 hours post infection.

**Average lifetime was calculated from Σf(d − 1)/n, where f is the number of mice that died on day d (surviving mice are included into f, and d is 16 in this case), n is the number of mice in the group.

TABLE 6

Weight change in animals infected with influenza virus Aichi/2/69 and treated with agent 1

| | Percent body weight change in days post infection | | | | | | | | |
|---|---|---|---|---|---|---|---|---|---|
| Dose of the agent | day 1 | day 2 | day 3 | day 4 | day 5 | day 7 | day 9 | day 11 | day 13 |
| Fullerene tris(aminocaproic acid) orally | | | | | | | | | |
| 100 mg/kg/day | +12 | +17 | +23 | +25 | +24 | +21 | +23 | +34 | +44 |
| 200 mg/kg/day | +15 | +20 | +23 | +25 | +24 | +22 | +25 | +45 | +57 |
| Fullerene tris(aminocaproic acid) intramuscularly | | | | | | | | | |
| 50 mg/kg/day | +9 | +14 | +21 | +26 | +30 | +27 | +38 | +64 | +74 |
| 100 mg/kg/day | +13 | +17 | +23 | +28 | +31 | +39 | +65 | +7 | +82 |
| 200 mg/kg/day | +11 | +20 | +26 | +35 | +39 | +43 | +51 | +62 | +70 |
| Fullerene tris(aminocaproic acid) intraperitoneally | | | | | | | | | |
| 50 mg/kg/day | +11 | +17 | +22 | +25 | +28 | +35 | +41 | +67 | +77 |
| 100 mg/kg/day | +9 | +15 | +19 | +21 | +21 | +27 | +37 | +50 | +82 |
| Virus Control | +18 | +16 | + | +1 | −8 | +3 | +56 | +72 | +74 |

TABLE 7

Protective activity of fullerene tris(aminocaproic acid) on experimental lethal pneumonia caused by Remantadine-resistant A/Puerto Rico/8/34 (H1N1) influenza virus

| Agent, dose 1 | Virus dose, LD$_{50}$ 2 | Number of animals in group 3 | Number of survivors 4 | Average lifetime (LD), days 5 | Mortality rate, % 6 | Index of protection, % 7 | Increase in LD, days 8 |
|---|---|---|---|---|---|---|---|
| Agent 1, 300 mg/kg | 10 | 14 | 8 | 11.3 | 42.9 | 49.4 | 3.2 |
| | 1 | 15 | 12 | 13.7 | 20.0 | 57.1 | 1.3 |
| | Summary dose | 29 | 20 | 12.5 | 31.0 | 51.7 | 2.2 |
| Agent 1, 100 mg/kg | 10 | 15 | 6 | 11.3 | 60.0 | 29.1 | 3.2 |
| | 1 | 15 | 12 | 13.9 | 20.0 | 57.1 | 1.6 |
| | Summary dose | 30 | 18 | 12.6 | 40.0 | 37.8 | 2.2 |
| Agent 1, 30 mg/kg | 10 | 15 | 4 | 10.4 | 73.3 | 13.3 | 2.3 |
| | 1 | 14 | 9 | 13.3 | 35.7 | 23.5 | 1.0 |
| | Summary dose | 29 | 13 | 11.8 | 55.2 | 14.2 | 1.4 |
| Remantadine | 10 | 15 | 4 | 9.7 | 73.3 | 13.3 | 1.6 |
| | 1 | 15 | 10 | 13.5 | 33.3 | 28.6 | 1.1 |
| | Summary dose | 30 | 14 | 11.6 | 53.3 | 17.0 | 1.2 |
| Tamiflu | 10 | 15 | 11 | 13.5 | 26.7 | 68.5 | 5.5 |
| | 1 | 13 | 11 | 14.4 | 15.4 | 67.0 | 2.1 |
| | Summary dose | 28 | 22 | 13.9 | 21.4 | 66.7 | 3.6 |
| Virus control | 10 | 13 | 2 | 8.1 | 84.6 | — | 0.0 |
| | 1 | 15 | 8 | 12.3 | 46.7 | — | 0.0 |
| | Summary dose | 28 | 10 | 10.4 | 64.3 | — | 0.0 |

TABLE 8

Protective activity of fullerene tris(aminocaproic acid) on experimental lethal influenza pneumonia caused by the A/swine/1976/31 (H1N1) influenza virus

| Agent, dose<br>1 | Virus dose,<br>$LD_{50}$<br>2 | Number of animals in group<br>3 | Number of survivors<br>4 | Average lifetime (LD), days<br>5 | Mortality rate, %<br>6 | Index of protection<br>7 | Increase in LD, days<br>8 |
|---|---|---|---|---|---|---|---|
| Agent 1, 300 mg/kg | 10 | 14 | 8 | 11.0 | 42.9 | 53.8 | 4.4 |
| | 1 | 14 | 11 | 13.6 | 21.4 | 59.8 | 3.0 |
| | Summary dose | 28 | 19 | 12.3 | 32.1 | 55.6 | 3.7 |
| Agent 1, 100 mg/kg | 10 | 13 | 6 | 10.3 | 53.8 | 42.0 | 3.7 |
| | 1 | 15 | 11 | 13.1 | 26.7 | 50.0 | 2.5 |
| | Summary dose | 28 | 17 | 11.8 | 39.3 | 45.7 | 3.1 |
| Agent 1, 30 mg/kg | 10 | 15 | 4 | 8.9 | 73.3 | 21.0 | 2.4 |
| | 1 | 15 | 9 | 12.3 | 40.0 | 25.0 | 1.7 |
| | Summary dose | 30 | 13 | 10.6 | 56.7 | 21.7 | 1.9 |
| Remantadine | 10 | 15 | 9 | 11.8 | 40.0 | 56.9 | 5.2 |
| | 1 | 15 | 13 | 14.3 | 13.3 | 75.0 | 3.7 |
| | Summary dose | 30 | 22 | 13.1 | 26.7 | 63.2 | 4.4 |
| Tamiflu | 10 | 13 | 8 | 11.0 | 38.5 | 58.6 | 4.4 |
| | 1 | 13 | 11 | 13.5 | 15.4 | 71.2 | 2.9 |
| | Summary dose | 26 | 19 | 12.2 | 26.9 | 62.8 | 3.6 |
| Virus control | 10 | 14 | 1 | 6.6 | 92.9 | — | 0.0 |
| | 1 | 15 | 7 | 10.6 | 53.3 | — | 0.0 |
| | Summary dose | 29 | 8 | 8.7 | 72.4 | — | 0.0 |

TABLE 9

Protective activity of fullerene tris(aminocaproic acid) on experimental lethal influenza pneumonia caused by Oseltamiv r-resistant A/Vladivostok/02/09 (H1N1) influenza virus

| Agent, dose<br>1 | Virus dose, $LD_{50}$<br>2 | Number of animals in group<br>3 | Number of survivors<br>4 | Average lifetime (LD), days<br>5 | Mortality rate, %<br>6 | Index of protection, %<br>7 | Increase in LD, days<br>8 |
|---|---|---|---|---|---|---|---|
| Agent 1, 300 mg/kg | 2 | 13 | 10 | 13.8 | 23.1 | 61.5 | 2.4 |
| | 0.4 | 13 | 12 | 14.5 | 7.7 | 71.8 | 1.4 |
| | Summary dose | 26 | 22 | 14.2 | 15.4 | 64.1 | 1.8 |
| Agent 1, 100 mg/kg | 2 | 12 | 8 | 13.3 | 33.3 | 44.4 | 1.9 |
| | 0.4 | 10 | 8 | 14.0 | 20.0 | 26.7 | 0.8 |
| | Summary dose | 22 | 16 | 13.6 | 27.3 | 36.4 | 1.3 |
| Agent 1, 30 mg/kg | 2 | 12 | 7 | 13.2 | 41.7 | 30.6 | 1.8 |
| | 0.4 | 13 | 11 | 14.2 | 15.4 | 43.6 | 1.0 |
| | Summary dose | 25 | 18 | 13.7 | 28.0 | 34.7 | 1.4 |
| Tamiflu | 2 | 10 | 5 | 11.7 | 50.0 | 16.7 | 0.3 |
| | 0.4 | 9 | 7 | 13.4 | 22.2 | 18.5 | 0.3 |
| | Summary dose | 19 | 12 | 12.5 | 36.8 | 14.0 | 0.2 |
| Remantadine | 2 | 13 | 12 | 14.6 | 7.7 | 87.2 | 3.2 |
| | 0.4 | 13 | 13 | 15.0 | 0.0 | 100.0 | 1.8 |
| | Summary dose | 26 | 25 | 14.8 | 3.8 | 91.0 | 2.5 |
| Virus control | 2 | 10 | 4 | 11.4 | 60.0 | — | 0.0 |
| | 0.4 | 11 | 8 | 13.2 | 27.3 | — | 0.0 |
| | Summary dose | 21 | 12 | 12.3 | 42.9 | — | 0.0 |

TABLE 10

Infectivity of influenza viruses in the lung tissue of white mice under administration of chemotherapeutics

| | Infectious virus titer ($\log_{10}EID_{50}$/20 mg tissue) for virus dose ($LD_{50}$) | | | | | |
|---|---|---|---|---|---|---|
| | A/Swine/1976/31 (H1N1) | | A/Puerto Rico/8/34 (H1N1) | | A/Vladivostok/2/09 (H1N1) | |
| Agent, dose | 1 | 5 | 1 | 5 | 0.4 | 2 |
| Agent 1, 300 mg/kg | 3.7 ± 0.3 | 4.1 ± 0.2 | 3.2 ± 0.3 | 4.1 ± 0.2 | 1.8 ± 0.2 | 2.9 ± 0.2 |
| Remantadine | 2.9 ± 0.2 | 3.4 ± 0.3 | 4.5 ± 0.2 | 5.1 ± 0.3 | 1.2 ± 0.2 | 2.0 ± 0.3 |
| Tamiflu | 3.1 ± 0.1 | 3.8 ± 0.3 | 2.2 ± 0.4 | 2.4 ± 0.3 | 2.5 ± 0.2 | 3.1 ± 0.3 |
| Virus control | 6.0 ± 0.0 | 6.4 ± 0.2 | 4.9 ± 0.3 | 5.5 ± 0.2 | 3.4 ± 0.4 | 4.0 ± 0.3 |

\* Difference from control is reliable for <0.05

TABLE 11

Infectivity of influenza viruses in the lung tissue of white mice under administration of chemotherapeutics

| | Size of chronic post-influenza pneumonia sites (% of the total surface area of the lungs) upon infecting with the virus (the lower of the doses used) | | |
|---|---|---|---|
| Agent | A/Swine/1976/3 1 (H1N1) | A/Puerto Rico/8/34 (H1N1) | A/Vladivostok/ 2/09 (H1N1) |
| Agent 1, 300 mg/kg | 25 ± 7 | 13 ± 3 | 7 ± 2 |
| Remantadine | 16 ± 5 | 32 ± 7 | 10 ± 2 |
| Tamiflu | 20 ± 5 | 15 ± 4; | 15 ± 5 |
| Virus control | 54 ± 7 | 41 ± 6 | 27 ± 8 |

\*Difference from control is reliable for $p < 0.05$

TABLE 12

Body weight dynamics in animals with Ehrlich ascites carcinoma treated by therapeutic agent

| Time post tumor transplantation, days | Animal body weight (g) Therapeutic agent used | | |
|---|---|---|---|
| | Agent 1 | Cisplatin | Therapeutic-free control |
| 1 | 18.6 ± 2.3 | 19.1 ± 5 | 19.2 ± 2.7 |
| 3 | 18.8 ± 2.2 | 19.3 ± 2.7 | 19.3 ± 2.7 |
| 5 | 18.8 ± 1.9 | 19.4 ± 2.5 | 19.5 ± 2.8 |
| 8 | 19.4 ± 1.7 | 19.8 ± 2.2 | 20.0 ± 2.7 |
| 10 | 19.9 ± 1.7 | 20.7 ± 2.4 | 20.8 ± 2.7 |
| 13 | 20.4 ± 1.5 | 21.4 ± 1.5 | 21.9 ± 2.6 |
| 15 | 20.4 ± 1.4\* | 21.8 ± 1.6 | 23.8 ± 2.2 |

\*Difference from agent-free control in the corresponding time is reliable for $p < 0.05$

TABLE 13

| | Percent amount of cells with the phenotype | | | | | | | |
|---|---|---|---|---|---|---|---|---|
| Agent | AnV$^-$7AAD$^-$ (living cells) | p | AnV$^+$ 7AAD$^-$ early apoptosis) | p | AnV$^+$ 7AAD$^+$ (late apoptosis) | p | AnV$^-$7AAD$^-$ (necrosis) | P |
| Agent 1 | 6.1 ± 6.2 | 0.00 | 31.1 ± 10.4 | 0.02 | 4.2 ± 2.4 | 0.17 | 0.4 ± 0.4 | 0.11 |
| Cisplatin | 55.2 ± 11.0 | 0.00 | 41.1 ± 11.3 | 0.00 | 3.5 ± 2.4 | 0.07 | 0.1 ± 0.2 | 0.03 |
| Agent-free control | 82.6 ± 7.7 | — | 9.7 ± 6.3 | — | 6.6 ± 2.9 | — | 1.0 ± 0.8 | — |

TABLE 14

Effect of agents on apoptosis in ascites Ehrlich carcinoma cells having large sizes and granularity in white mice

| | Процентклеток с фенотипом | | | | | | | |
|---|---|---|---|---|---|---|---|---|
| Agent | AnV$^-$7AAD$^-$ (living cells) | p | AnV$^+$ 7AAD$^-$ (early apoptosis) | p | AnV$^+$ 7AAD$^+$ (late apoptosis) | p | AnV$^-$7AAD$^+$ (necrosis) | p |
| Agent 1 | 0.3 ± 0.1 | 0.00 | 0.1 ± 0.1 | 0.02 | 69.5 ± 5.8 | 0.00 | 30.2 ± 5.9 | 0.00 |
| Cisplatin | 0.4 ± 0.2 | 0.00 | 0.3 ± 0.3 | 0.02 | 72.8 ± 10.9 | 0.00 | 26.6 ± 11.1 | 0.01 |
| Agent-free control | 89.6 ± 7.3 | — | 3.6 ± 2.8 | — | 6.7 ± 4.8 | — | 0.2 ± 0.2 | — |

TABLE 15

Table 15. Ehrlich carcinoma solid tumor size dynamics in
white mice treated with the therapeutic agents under study

| Agent, dose (mg/kg Beca) | Tumor size (mm$^3$), days post transplantation пересадки | | | | | |
|---|---|---|---|---|---|---|
| | 8 | 13 | 17 | 21 | 24 | 28 |
| Control | 156.6 | 711.7 | 1250.3 | 1902.1 | 2296.5 | 2888.2 |
| Agent 1, 300 | 72.7 | 416.3 | 1224.6 | 1703.4 | 2048.5 | 2525.7 |
| Agent 1, 100 | 72.5 | 544.3 | 693.6 | 1250.8 | 1654.3 | 2239.8 |
| Cisplatin | 56.5 | 249.2 | 464.3 | 1071.9 | 1743.3 | 1269.4 |

* Difference from agent-free control is reliable for $p < 0.05$.

Example 9

Chronic Toxicity of Fullerene Tris(Aminocaproic Acid) Hydrate in Rats with Intramuscular Administration During 30 Days The experiment was carried out at the Research Center for Toxicology and Hygienic Regulation on bioagents (FGUN NITs TBP FMBA of Russia), the town of Serpukhov.

The task of these studies was an experimental evaluation of the level and character of a possible damaging effect of fullerene tris(aminocaproic acid) hydrate on rat's body with intramuscular administration during 30 days.

The experiments were carried out on Wistar rats, purchased at the nursery of GU NTsBT, the Russian Academy of Medical Sciences (Stolbovaya branch). The maintenance of animals met sanitary regulations approved by the Ministry of Public Health of the USSR, Jul. 6, 1973, on the organization, equipment, and maintenance of experimental and biological clinics (vivariums). Animals were fed with natural and briquetted foods in accordance with the standards adopted by the order no. 755 of the Ministry of Public Health of the USSR, Aug. 12, 1977. The animals were quarantined and acclimatized in a vivarium for 5 days.

Experimental animal groups were formed by random sampling with the body weight as a leading indicator.

The tested substance was administered to rats intramuscularly daily during 30 days in doses of 3, 9, or 20 mg/kg as solutions of various concentrations in 20% dimethyl sulfoxide (DMSO) solution. Control group animals received 20% DMSO solution. Working solutions of the substance and DMSO were prepared every day immediately before use. The dose amounts to be administered were corrected taking into account individual's body weight after each weighing. Each dose was tested in 20 animals (10 males and 10 females).

In order to evaluate the toxic effect of fullerene tris(aminocaproic acid) hydrate, 24 hours after the end of the administration period of the substance, one half the animals in each group were taken out of the experiment for hematological, biochemical, and pathological studies. The other half of the experimental animals were taken out of the experiment after the period of withdrawal of the substance, and similar studies were carried out.

During the period of administration of the substance and for 14 days after withdrawal of administration, the general condition and the clinical symptoms of intoxication in animals were evaluated daily. The general condition of an animal was evaluated for its physical activity, food and water consumption, condition of wool and visible mucous membranes, and body weight.

Hematological analysis was performed using a Hemascreen 13 (Hospitex Diagnostics, Italy) semiautomatic two-channel conductometric cell counter and using optical microscopy.

Biochemical values of blood serum were determined on a Stat Fax 3300 semi-automatic analyzer.

Biochemical values of urea were determined on a Urisys 1100 semi-automatic analyzer.

The morphological status of the viscera of animals was determined visually at autopsy and microscopic histological examination of samples (4- to 5-micron paraffin sections stained with hematoxylin and eosin).

Statistical processing of the results was carried out by variation statistics methods using Student's test.

1. The Results of Studies.

1.1. The Results of Clinical Observation.

Rats were intramuscularly injected with fullerene tris(aminocaproic acid) hydrate in doses of 3, 9, or 20 mg/kg for a month daily. At all doses, no clinical signs of poisoning were observed; \ the animals in the experimental and control groups did not differ from one another in their general condition. Body weight gain in rats throughout the experiment in the experimental groups was not significantly different from the control (Table 16).

TABLE 16

Body weight in rats in the periods of administration and withdrawal of fullerene tris(aminocaproic acid) hydrate

| Observation day | DMSO control | Fullerene tris(aminocaproic acid) hydrate, mg/kg | | |
|---|---|---|---|---|
| | | 3 | 9 | 20 |
| Males (M ± m) | | | | |
| 0 | 196.6 ± 3.3 | 193.6 ± 3.4 | 196.6 ± 4.2 | 193.4 ± 4.1 |
| 7 | 231.8 ± 4.4 | 224.6 ± 5.2 | 233.6 ± 7.4 | 227.0 ± 5.0 |
| 14 | 271.4 ± 5.3 | 255.6 ± 6.9 | 270.4 ± 10.6 | 266.6 ± 5.7 |
| 21 | 291.0 ± 5.3 | 273.6 ± 7.6 | 290.0 ± 14.4 | 288.2 ± 6.8 |
| 28 | 314.4 ± 5.9 | 291.2 ± 9.5 | 307.6 ± 15.9 | 306.6 ± 8.1 |
| 35 | 336.0 ± 10.2 | 307.2 ± 14.9 | 346.4 ± 13.7 | 333.6 ± 8.7 |
| 42 | 342.8 ± 13.2 | 315.6 ± 16.8 | 360.4 ± 12.1 | 349.6 ± 9.5 |
| Males (M ± m) | | | | |
| 0 | 176.0 ± 3.2 | 179.6 ± 3.6 | 180.4 ± 3.4 | 175.4 ± 4.0 |
| 7 | 192.4 ± 4.9 | 192.6 ± 4.5 | 197.0 ± 4.9 | 192.8 ± 4.0 |
| 14 | 212.4 ± 6.0 | 210.8 ± 4.9 | 215.2 ± 6.0 | 213.0 ± 3.7 |
| 21 | 222.4 ± 6.7 | 223.8 ± 5.1 | 227.4 ± 5.7 | 221.6 ± 3.8 |
| 28 | 237.6 ± 6.6 | 234.4 ± 4.0 | 240.2 ± 6.1 | 234.4 ± 4.4 |
| 35 | 250.0 ± 12.7 | 251.6 ± 6.0 | 254.4 ± 12.7 | 246.8 ± 7.2 |
| 42 | 252.8 ± 13.3 | 258.8 ± 5.1 | 260.4 ± 12.3 | 253.6 ± 5.6 |

1.2. The Results of the Biochemical Analysis of Blood Serum

After the end of administration of fullerene tris(aminocaproic acid) hydrate a significant reduction was demonstrated in urea level at the maximum dose tested in male rats (Table 17). The shown changes in cholesterol concentration at the minimum and moderate doses are not associated with the effect of the investigated substance and do not exceed the physiological limits. In female rats a slight but reliable increase in alanine amino transferase activity was shown at the maximum tested dose. The changes found in glucose level at the minimal dose and in total protein and cholesterol concentrations at the moderate dose of the substance do not have dose response and do not go beyond the physiological limits.

TABLE 17

Biochemical values of blood serum in rats after administration fullerene tris(aminocaproic acid) hydrate

| Parameter, units of measure | Control (DMSO) | Fullerene tris(aminocaproic acid) hydrate, mg/kg | | |
|---|---|---|---|---|
| | | 3 | 9 | 20 |
| 1 | 2 | 3 | 4 | 5 |
| *Males (M ± m)* | | | | |
| Total protein, g/L | 95.6 ± 9.59 | 86.88 ± 5.28 | 102.1 ± 34.65 | 82.08 ± 9.28 |
| Glucose, mmol/L | 6.28 ± 0.29 | 6.88 ± 0.73 | 6.4 ± 1.02 | 7.0 ± 1.26 |
| Urea, mmol/L | 12.94 ± 1.77 | 10.66 ± 2.89 | 11.36 ± 2.71 | 9.22 ± 1.56* |
| Cholesterol, mmol/L | 5.42 ± 0.71 | 4.17 ± 0.68* | 3.88 ± 0.75* | 4.96 ± 1.03 |
| Bilirubin, Mcmol/L | 8.96 ± 2.84 | 9.98 ± 1.67 | 9.16 ± 1.4 | 8.76 ± 1.54 |
| Creatinine, mcmol/L | 75.36 ± 8.81 | 85.58 ± 17.46 | 82.06 ± 21.99 | 75.6 ± 15.51 |
| ALT, Units/L | 15.52 ± 3.17 | 17.12 ± 1.2 | 14.62 ± 4.22 | 14.04 ± 3.01 |
| AST, Units/L | 28.56 ± 5.94 | 25.18 ± 3.95 | 29.34 ± 3.8 | 24.44 ± 5.48 |
| Alkali phosphatase, Units/L | 343 ± 89 | 333 ± 48 | 300 ± 56 | 28.3 ± 67 |
| *Females (M ± m)* | | | | |
| Total protein, g/L | 79.0 ± 7.18 | 81.64 ± 11.03 | 68.94 ± 2.97* | 83.16 ± 11.75 |
| Glucose, mmol/L | 5.64 ± 0.72 | 7.64 ± 1.56* | 6.36 ± 0.67 | 6.46 ± 0.51 |
| Urea, mmol/L | 9.88 ± 1.8 | 8.0 ± 4.04 | 10.02 ± 1.46 | 9.48 ± 1.86 |
| Cholesterol, mmol/L | 3.66 ± 0.34 | 4.11 ± 0.45 | 4.42 ± 0.56* | 4.16 ± 0.88 |
| Bilirubin, Mcmol/L | 7.52 ± 2.86 | 10.96 ± 2.14 | 9.46 ± 2.26 | 7.18 ± 0.95 |
| Creatinine, mcmol/L | 70.1 ± 16.19 | 56.44 ± 3.3 | 52.46 ± 5.77 | 53.78 ± 8.31 |
| ALT, Units/L | 10.52 ± 1.01 | 10.7 ± 1.57 | 12.52 ± 2.11 | 13.52 ± 1.4* |
| AST, Units/L | 22.75 ± 1.37 | 27.51 ± 5.11 | 24.02 ± 2.64 | 21.47 ± 3.09 |
| Alkali hosphatase, Units/L | 227 ± 191 | 143 ± 47 | 159 ± 28 | 248 ± 107 |

*Statistically reliable according to Student's-test.

A reliable decrease in creatinine concentration at the maximal tested dose was shown after the withdrawal period of fullerene tris(aminocaproic acid) hydrate in male and female rats. At the same dose, a change in aspartate amino transferase activity was shown in both male and female rats; in males, however, this was a decrease in activity, while in females this was an increase in activity (Table 8).

TABLE 18

Biochemical values of blood serum in rats after withdrawal of administration of fullerene tris(aminocaproic acid)hydrate

| Parameter, units of measure | Control (DMSO) | Fullerene tris(aminocaproic acid) hydrate, mg/kg | | |
|---|---|---|---|---|
| | | 3 | 9 | 20 |
| 1 | 2 | 3 | 4 | 5 |
| *Males (M ± m)* | | | | |
| Total protein, g/L | 70.08 ± 7.11 | 67.20 ± 7.60 | 68.06 ± 7.27 | 66.58 ± 2.67 |
| Glucose, mmol/L | 6.04 ± 0.56 | 6.54 ± 1.03 | 7.18 ± 0.80* | 6.40 ± 0.93 |
| Urea, mmol/L | 7.52 ± .74 | 7.96 ± 1.05 | 7.14 ± 1.59 | 8.52 ± 0.99 |
| Cholesterol, mmol/L | 4.70 ± 0.88 | 4.06 ± 0.25 | 4.25 ± 0.72 | 4.57 ± 0.54 |
| Bilirubin, mcmol/L | 15.72 ± 7.74 | 20.32 ± 5.19 | 16.06 ± 2.72 | 17.30 ± 2.11 |
| Creatinine, mcmol/L | 57.46 ± 12.35 | 51.10 ± 7.11 | 48.12 ± 10.16 | 41.86 ± 4.09* |
| ALT, Units/L | 22.44 ± 2.31 | 21.18 ± 5.54 | 21.52 ± 2.68 | 24.38 ± 2.22 |
| AST, Units/L | 19.53 ± 2.04 | 18.18 ± 1.39 | 18.08 ± 2.64 | 16.18 ± 1.83* |
| Alkali phosphatase, Units/L | 258 ± 46 | 263 ± 71 | 255 ± 48 | 238 ± 61 |

TABLE 18-continued

Biochemical values of blood serum in rats after withdrawal of administration of fullerene tris(aminocaproic acid)hydrate

| Parameter, units of measure | Control (DMSO) | Fullerene tris(aminocaproic acid) hydrate, mg/kg | | |
|---|---|---|---|---|
| | | 3 | 9 | 20 |
| 1 | 2 | 3 | 4 | 5 |
| | Females (M ± m) | | | |
| Total proten, g/L | 70.92 ± 10.67 | 71.12 ± 6.66 | 78.48 ± 8.94 | 72.76 ± 8.11 |
| Glucose, mmol/L | 6.82 ± 1.32 | 7.62 ± 0.69 | 6.78 ± 0.97 | 6.90 ± 1.23 |
| Urea, mmol/L | 8.46 ± 1.15 | 7.20 ± 2.43 | 7.94 ± 1.25 | 9.4 ± 2.93 |
| Cholesterol, mmol/L | 4.49 ± 0.95 | 4.26 ± 1.04 | 5.02 ± 1.7 | 5.67 ± 1.2 |
| Bilirubin, mcmol/L | 11.9 ± 5.65 | 13.0 ± 3.07 | 11.8 ± 1.18 | 11.28 ± 1.91 |
| Creatinine, mcmol/L | 74.14 ± 18.21 | 63.76 ± 16.67 | 55.84 ± 9.94 | 50.26 ± 5.04 |
| ALT, Units/L | 16.52 ± 3.23 | 14.36 ± 5.02 | 14.44 ± 2.86 | 17.82 ± 3.11 |
| AST, Units/L | 14.29 ± 2.5 | 16.84 ± 1.27 | 17.68 ± 2.87 | 18.41 ± 2.85* |
| Alkali phosphatase, Units/L | 219 ± 58 | 168 ± 54 | 218 ± 44 | 221 ± 36 |

*Statistically reliable according to Student's t-test.

Evaluating the results of biochemical analysis of blood serum of rats during the administration of the substance and after the period of administration withdrawal, it should be noted that the values of the above changes in serum in male and female rats are within the limits of the physiological range for the species.

1.3. The Results of Hematological Analysis of Blood

After the end of fullerene tris(aminocaproic acid) hydrate administration, no changes in hematological values were found to be associated with the tested substance. In female rats, an insignificant reduction in mean erythrocyte volume at the moderate dose and some increase in reticulocytes fraction at the minimal dose were observed (Table 19). These changes do not extend beyond the physiological range and do not have dose response.

TABLE 19

Hematological values in rat blood after the end of administration of tris(aminocaproic acid) hydrate

| Parameter, units of measure | Control (DMSO) | Fullerence tris(aminocaproic acid) hydrate, mg/kg | | |
|---|---|---|---|---|
| | | 3 | 9 | 20 |
| 1 | 2 | 3 | 4 | 5 |
| | Males (M ± m) | | | |
| Hemoglobin, mol/dm$^3$ | 8.4 ± 0.8 | 7.8 ± 0.3 | 8.1 ± 1.6 | 8.0 ± 1.0 |
| Erythrocytes, Mln/mm$^3$ | 5.7 ± 1.0 | 6.0 ± 0.6 | 6.0 ± 0.9 | 6.3 ± 0.7 |
| Hematocrit, % | 32.3 ± 7.1 | 35.4 ± 3.4 | 35.0 ± 5.3 | 35.3 ± 4.3 |
| Avg. erythr. volume., mcm$^3$ | 57.0 ± 5.1 | 59.0 ± 2.7 | 58.2 ± 4.5 | 55.6 ± 1.5 |
| Reticulocytes, % | 3.8 ± 0.8 | 4.0 ± 0.6 | 3.8 ± 0.9 | 4.4 ± 0.8 |
| Thrombocytes, ths | 692.6 ± 93.7 | 692.6 ± 98.2 | 699.8 ± 181.2 | 766.2 ± 85.1 |
| Leukocytes, ths/mm, including: | 22.9 ± 4.1 | 22.8 ± 1.5 | 24.6 ± 5.2 | 23.3 ± 3.8 |
| Basophils, % | 0 | 0 | 0 | 0 |
| Eosinophils, % | 0.8 ± 1.1 | 0.8 ± 1.1 | 1.0 ± 1.2 | 0.8 ± 1.1 |
| Young, % | 0 | 0 | 0 | 0 |
| Stabnuclear, % | 1.6 ± 1.7 | 1.6 ± 0.9 | 1.0 ± 1.2 | 1.2 ± 1.1 |
| Segmentonuclear, % | 24.4 ± 3.6 | 28.4 ± 7.8 | 21.5 ± 4.4 | 24.4 ± 3.8 |
| Lymphocytes, % | 67.6 ± 5.0 | 64.8 ± 5.8 | 71.0 ± 2.6 | 68.0 ± 5.1 |
| Monocytes, % | 5.6 ± 2.2 | 4.8 ± 2.3 | 5.5 ± 1.9 | 5.6 ± 0.9 |
| | Females (M ± m) | | | |
| Hemoglobin, mol/dm$^3$ | 8.0 ± 0.2 | 7.7 ± 0.6 | 7.8 ± 0.9 | 8.1 ± 1.0 |
| Erythrocytes, Mln/mm$^3$ | 5.4 ± 0.6 | 6.0 ± 0.8 | 6.3 ± 0.7 | 6.3 ± 0.8 |
| Hematocrit, % | 32.0 ± 2.3 | 32.8 ± 5.2 | 34.4 ± 3.2 | 35.7 ± 4.0 |

TABLE 19-continued

Hematological values in rat blood after the end of administration of tris(aminocaproic acid) hydrate

| Parameter, units of measure | Control (DMSO) | Fullerence tris(aminocaproic acid) hydrate, mg/kg | | |
|---|---|---|---|---|
| | | 3 | 9 | 20 |
| 1 | 2 | 3 | 4 | 5 |
| Avg. erythr. volume., mcm³ | 59.6 ± 3.1 | 57.8 ± 5.0 | 55.0 ± 1.9* | 57.4 ± 3. |
| Reticulocytes, % | 5.1 ± 0.5 | 6.6 ± 0.5* | 4.9 ± 0.3 | 4.8 ± 0.3 |
| Thrombocytes, ths | 538.4 ± 126.8 | 439.0 ± 104.0 | 505.0 ± 75.7 | 542.4 ± 91.2 |
| Leukocytes ths/mm³, including: | 21.7 ± 8.4 | 21.4 ± 4.7 | 20.4 ± 8.8 | 19.7 ± 3.2 |
| Basophils, % | 0 | 0 | 0 | 0 |
| Eosinophils, % | 1.6 ± 1.7 | 2.0 ± 2.0 | 2.0 ± 2.4 | 1.2 ± 1.1 |
| Young, % | 0 | 0 | 0 | 0 |
| Stabnuclear, % | 2.0 ± 1.4 | 1.2 ± 1.1 | 0.8 ± 1.1 | 1.6 ± 0.9 |
| Segmentonuclear, % | 21.2 ± 5.0 | 20.8 ± 5.4 | 18.8 ± 5.0 | 18.4 ± 3.6 |
| Lymphocytes, % | 69.8 ± 3.3 | 70.4 ± 4.6 | 72.4 ± 5.2 | 73.2 ± 4.1 |
| Monocytes, % | 5.4 ± 0.9 | 5.6 ± 1.7 | 6.0 ± 1.4 | 5.6 ± 0.9 |

*Statistically reliable according to Student's t-test.

Studies of the hematological values in rats after the end of the fullerene tris(aminocapric acid) hydrate withdrawal period did not show reliable differences between the control and experimental animals (Table 20).

TABLE 20

Hematological values in rat blood after withdrawal of tris(aminocaproic acid) hydrate administration

| Parameter, units of measure | Control (DMSO) | Fullerene tris(aminocaproic acid) hydrate, mg/kg | | |
|---|---|---|---|---|
| | | 3 | 9 | 20 |
| 1 | 2 | 3 | 4 | 5 |
| Males (M ± m) | | | | |
| Hemoglobin, mol/dm³ | 7.9 ± 0.7 | 8.3 ± 3.7 | 7.9 ± 0.3 | 7.4 ± 0.8 |
| Erythrocytes, Mln/mm | 6.3 ± 0.6 | 6.5 ± 1.2 | 6.4 ± 0.5 | 6.3 ± 0.8 |
| Hematocrit, % | 33.0 ± 2.6 | 33.7 ± 1.7 | 34.1 ± 2.1 | 31.2 ± 3.5 |
| Avg. erythr. volume., mcm | 52.8 ± 2.5 | 52.0 ± 1.6 | 53.4 ± 4.6 | 50.4 ± 1.5 |
| Reticulocytes, % | 4.0 ± 0.6 | 4.3 ± 1.1 | 4.0 ± 0.3 | 4.2 ± 0.5 |
| Thrombocytes, ths | 496.6 ± 48.9 | 445.6 ± 55.8 | 479.8 ± 43.8 | 447.0 ± 86.9 |
| Leukocytes, ths/mm³, including: | 22.5 ± 3.6 | 22.0 ± 6.8 | 19.6 ± 2.5 | 24.8 ± 6.2 |
| Basophils, % | 0 | 0 | 0 | 0 |
| Eosinophils, % | 0.8 ± 1.1 | 0.8 ± 1.1 | 0.8 ± 1.1 | 0.8 ± 1.1 |
| Young, % | 0 | 0 | 0 | 0 |
| Stabnuclear, % | 1.6 ± 1.7 | 1.6 ± 0.9 | 1.6 ± 1.7 | 1.2 ± 1.1 |
| Segmentonuclear, % | 24.4 ± 3.6 | 28.4 ± 7.8 | 21.6 ± 3.8 | 24.4 ± 3.8 |
| Lymphocytes, % | 67.6 ± 5.0 | 64.8 ± 5. | 71.0 ± 2.2 | 68.0 ± 5.1 |
| Monocytes, % | 5.6 ± 2.2 | 4.8 ± 2.3 | 5.0 ± 2.0 | 5.6 ± 0.9 |
| Females (M ± m) | | | | |
| Hemoglobin, mol/dm³ | 8.1 ± 0.6 | 7.7 ± 0.7 | 8.2 ± 0.3 | 8.5 ± 0.6 |
| Erythrocytes, Mln/mm³ | 5.9 ± 0.7 | 5.8 ± 0.3 | 6.3 ± 0.5 | 6.4 ± 0.6 |
| Hematocrit, % | 31.7 ± 3.8 | 32.3 ± 3.2 | 32.9 ± 2.0 | 32.9 ± 2.2 |
| Avg. erythr. volume., Mcm | 54.4 ± 1.7 | 55.2 ± 4.6 | 52.4 ± 1.5 | 52.2 ± 3.4 |
| Reticulocytes, % | 4.6 ± 0.6 | 4.4 ± 0.5 | 4.3 ± 0.5 | 4.5 ± 0.4 |
| Thrombocytes, ths | 459.8 ± 86.0 | 462.4 ± 95.1 | 453.0 ± 67.3 | 470.8 ± 34.8 |
| Leukocytes, ths/mm, including: | 21.6 ± 2.6 | 17.8 ± 4.0 | 20.1 ± 3.5 | 8.1 ± 2.5 |
| Basophils, % | 0 | 0 | 0 | 0 |
| Eosinophils, % | 2.0 ± 1.4 | 1.8 ± 1.8 | 1.8 ± 1.8 | 2.0 ± 1.4 |
| Young, % | 0 | 0 | 0 | 0 |
| Stabnuclear, % | 1.4 ± 1.3 | 1.6 ± 1.7 | 1.2 ± 1.1 | 1.4 ± 1.3 |
| Segmentonuclear, % | 20.8 ± 3.3 | 22.0 ± 2.4 | 22.0 ± 3.2 | 22.8 ± 3.8 |

TABLE 20-continued

Hematological values in rat blood after withdrawal of tris(aminocaproic acid) hydrate administration

| Parameter, units of measure | Control (DMSO) | Fullerene tris(aminocaproic acid) hydrate, mg/kg | | |
|---|---|---|---|---|
| | | 3 | 9 | 20 |
| 1 | 2 | 3 | 4 | 5 |
| Lymphocytes, % | 70.6 ± 3.7 | 69.2 ± 3. | 69.4 ± 4.4 | 68.4 ± 4.1 |
| Monocytes, % | 5.2 ± 1.3 | 5.4 ± 0.9 | 5.6 ± 1.1 | 5.4 ± 0.9 |

1.4. The Analysis of Urine

After the end of the period of fullerene tris(aminocaproic acid) hydrate administration, an increase of urinary pH was found in the group of males at a dose of 9 mg/kg (Table 21). The new value level is within the physiological range; no dose dependence is observed.

After the period of fullerene tris(aminocaproic acid) hydrate withdrawal, a reduction in relative urine density was noticed in the female group at a dose of 20.0 mg/kg compared to the control group animals. In male groups, statistically reliable changes were observed in the same period compared to the control group, namely: at a dose of 3.0 mg/kg, an increase in pH; and at a dose of 9.0 mg/kg, an increase in relative urine density. Both values are within the limits of physiological range and do not have dose response (Table 22).

TABLE 21

Urine values in rats after the end of fullerene tris(aminocaproic acid) hydrate administration

| | | | Number of animals with values going beyond the limits | | | | | | | |
|---|---|---|---|---|---|---|---|---|---|---|
| Dose (mg/kg) | Relative density | pH | Leukocytes cells/mcL | Nitrites, mcmol/L | Protein, g/L | Glucose, mmol/L | Ketone bodies, mmol/L | Urobilinogen, mcmol/L | Bilirubin, mcmol/L | Erythrocytes, cells/mcL |
| Males | | | | | | | | | | |
| 0 | 1.023 ± 0.005 | 6.3 ± 0.4 | 2 | 1 | 4 | 0 | 4 | 2 | 1 | 5 |
| 3.0 | 1.024 ± 0.005 | 6.3 ± 0.7 | 3 | 3 | 5 | 0 | 4 | 4 | 1 | 5 |
| 9.0 | 1.016 ± 0.006 | 6.9 ± 0.2* | 4 | 1 | 3 | 1 | 2 | 0 | 0 | 5 |
| 20.0 | 1.023 ± 0.004 | 6.3 ± 0.7 | 5 | 1 | 4 | 0 | 2 | 2 | 0 | 5 |
| Females | | | | | | | | | | |
| 0 | 1.019 ± 0.006 | 6.6 ± 0.2 | 3 | 2 | 2 | 0 | 0 | 0 | 0 | 4 |
| 3.0 | 1.020 ± 0.003 | 6.6 ± 0.2 | 3 | 1 | 1 | 0 | 1 | 1 | 0 | 4 |
| 9.0 | 1.017 ± 0.007 | 6.8 ± 0.2 | 2 | 3 | 3 | 0 | 0 | 1 | 1 | 4 |
| 20.0 | 1.016 ± 0.008 | 6.4 ± 0.5 | 2 | 1 | 1 | 0 | 1 | 0 | 0 | 5 |

* Statistically reliable according Student's t-test

TABLE 22

Urine values in rats after withdrawal of fullerene tris(aminocaproic acid) hydrate administration

| | | | Number of animals with values going beyond the limits | | | | | | | |
|---|---|---|---|---|---|---|---|---|---|---|
| Dose (mg/kg) | Relative density | pH | Leukocytes cells/mcL | Nitrites, mcmol/L | Protein, g/L | Glucose, mmol/L | Ketone bodies, mmol/L | Urobilinogen, mcmol/L | Bilirubin, mcmol/L | Erythrocytes, cells/mcL |
| Males | | | | | | | | | | |
| 0 | 1.019 ± 0.005 | 6.0 ± 0.0 | 1 | 0 | 2 | 0 | 0 | 0 | 0 | 4 |
| 3.0 | 1.001 ± 0.005 | 6.6 ± 0.4* | 3 | 0 | 2 | 0 | 0 | 0 | 0 | 5 |
| 9.0 | 1.025 ± 0.001* | 5.6 ± 0.5 | 4 | 0 | 5 | 0 | 4 | 4 | 0 | 5 |
| 20.0 | 1.027 ± 0.014 | 6.0 ± 0.6 | 4 | 0 | 3 | 0 | 2 | 2 | 0 | 5 |
| Females | | | | | | | | | | |
| 0 | 1.020 ± 0.007 | 6.2 ± 1.3 | 1 | 0 | 3 | 0 | 0 | 0 | 0 | 1 |
| 3.0 | 1.001 ± 0.005 | 7.2 ± 0.4 | 2 | 0 | 1 | 0 | 0 | 0 | 0 | 3 |
| 9.0 | 1.019 ± 0.008 | 6.1 ± 1.0 | 2 | 0 | 1 | 0 | 2 | 0 | 0 | 2 |
| 20.0 | 1.008 ± 0.002* | 7.0 ± 0.0 | 1 | 0 | 0 | 0 | 0 | 0 | 0 | 4 |

*Statistically reliable according Student's t-test

1.5. Findings of Pathomorphological Studies

At autopsy conducted after the end of the fullerene tris (aminocaproic acid) hydrate intramuscular administration period, the external examination and study did not show differences between the experimental and control group rats: wool cover was smooth and shiny; skin was elastic and mobile; subcutaneous tissue was moderate; the visible mucous membrane was pale, pure, without ulceration and foreign overlays; and abnormal discharge from the body's orifices were absent. When the chest and abdominal cavities were open, the anatomically correct positioning of the internal organs was observed. Macroscopically distinct signs of pathology of the viscera were not detected. When the skeletal muscles of the back-femoral group (injection site) was dissected in animals that received fullerene tris(aminocaproic acid) hydrate at any of the tested doses, a brownish color of muscle tissue, fascia, and fat layers was noticed. In control group animals, the aforementioned tissues had no this color.

In analyzing the weight coefficients of viscera of animals after the period of fullerene tris(aminocaproic acid) hydrate intramuscular administration, no distinctions between the rats of the experimental groups and the control group (Table 23).

hydrate at the maximal dose and the control group rats. In examination, separate pathological changes were found primarily in the lungs, liver and kidneys (Table 24). The degree of detected change slightly varied within groups, but was generally weak or moderate. Given the lack of any alternative or proliferative response in areas of detected changes in the organs, and a large number of cases of acute plethora of blood vessels in them, the most likely cause of their appearance is the individual responses of animals to general anesthesia and inhalation of carbon dioxide in the euthanasia. Based on a roughly equal frequency of occurrence of established lesions in the experimental and control groups, we can conclude that their induction by the tested substance is absent. Therefore, these changes are considered as background.

At the site of injection of fullerene tris(aminocaproic acid) hydrate (skeletal muscle), found were both inflammatory changes (small hemorrhage sites, muffled and swollen muscle fibers sites, infiltration by lymphoid cells of the space between the individual muscle fibers and fiber bundles) and regenerative changes (areas of loose or dense connective tissue with newly formed vessels). These changes were also intrinsic to the control group rats. The above picture is char-

TABLE 23

Weight coefficients of viscera of rats after the peroid of fullerene tris(aminocaproic acid) hydrate intramuscular administration

| Dose, mg/kg | Weight coefficients of viscera, g/kg body weight | | | | | | |
|---|---|---|---|---|---|---|---|
| | heart | lungs | liver | spleen | kidney | thymus | Testicles |
| Males | | | | | | | |
| 0 | 4.3 ± 0.4 | 8.9 ± 1.3 | 36.5 ± 3.3 | 6.1 ± 1.6 | 7.1 ± 0.2 | 1.8 ± 0.2 | 11.1 ± 1.0 |
| 3.0 | 4.0 ± 0.7 | 8.3 ± 1.7 | 35.8 ± 1.8 | 6.0 ± 0.7 | 7.1 ± 0.7 | 1.6 ± 0.4 | 10.4 ± 1.3 |
| 9.0 | 3.8 ± 0.6 | 8.3 ± 1.4 | 36.6 ± 4.8 | 6.3 ± 0.7 | 7.2 ± 0.3 | 1.3 ± 0.5 | 9.7 ± 1.1 |
| 20.0 | 4.3 ± 0.3 | 8.6 ± 0.3 | 39.8 ± 4.4 | 5.8 ± 1.8 | 7.6 ± 0.4 | 1.4 ± 0.4 | 11.1 ± 0.9 |
| Females | | | | | | | |
| 0 | 3.8 ± 0.5 | 9.3 ± 1.0 | 39.9 ± 2.1 | 6.3 ± 1.8 | 7.3 ± 0.5 | 2.2 ± 0.6 | — |
| 3.0 | 3.9 ± 0.7 | 9.4 ± 1.0 | 37.9 ± 2.5 | 6.7 ± 1.0 | 7.8 ± 0.5 | 1.9 ± 0.3 | — |
| 9.0 | 3.8 ± 0.6 | 9.9 ± 0.7 | 39.8 ± 2.9 | 6.6 ± 0.8 | 7.8 ± 0.5 | 1.6 ± 0.5 | — |
| 20.0 | 3.8 ± 0.6 | 10.1 ± 1.5 | 43.0 ± 4.1 | 6.6 ± 1.3 | 8.6 ± 0.8 | 1.6 ± 0.7 | — |

Microscopic examination involved a comparative evaluation of the histopathological picture of organs and tissues of the animals that received fullerene tris(aminocaproic acid) acteristic of multiple injuries as a result of repeated intramuscular injections, in this study regardless of the administered substance.

TABLE 24

Results of microscopic examination of morphologic changes in organs and tissues of rats after 30 days of intramuscular administration of fullerene tris(aminocaproic acid) hydrate

| Substance | | Solvent | | | Fullerene tris(aminocaproic acid) | | |
| --- | --- | --- | --- | --- | --- | --- | --- |
| Dose (mg/kg) | | 0 | | | 20 | | |
| Gender | | Males | | Females | | Males | | Females |
| Number of animals in group | | 5 | | 5 | | 5 | | 5 |
| Number of survivors | | 5 | | 5 | | 5 | | 5 |
| Organ/ tissue | Morphological changes | Animals with changes | | | | | | |
| | | Ind. No | Number | Ind.No | Number | Ind. No | Number | Ind. No | Number |
| Lung | Thickening of the interalveolar septa (total) | 11, 12 | 2 | 2, 5 | 2 | — | — | — | — |
| | Thickening of the interalveolar septa (sites) | 14, 15 | 2 | 4 | 1 | 72, 74 | 2 | 61, 62 | 2 |
| | Foci of infiltration of interalveolar septa with lymphoid cells, macrophages | 11 | 1 | — | — | 72 | 1 | 61, 62 | 2 |
| | Narrowing of the bronchial tubes | 11, 12, 13, 14, 15 | 5 | 2, 4, 5 | 3 | 74 | 1 | — | — |
| | Plethora of blood vessels | 12, 13, 14, 15 | 4 | 1 | — | 72, 73, 74, 75 | 4 | 62, 64, 65 | 3 |

TABLE 24-continued

Results of microscopic examination of morphologic changes in organs and tissues of rats after 30 days of intramuscular administration of fullerene tris(aminocaproic acid) hydrate

| | | | | | | | | | |
|---|---|---|---|---|---|---|---|---|---|
| | Plethora of alveolar capillaries | 12, 13, 14, 15 | 4 | — | — | 74, 75 | 2 | 61 | 1 |
| | Perivascular lymphoid infiltration | 11, 13 | 2 | 2 | 1 | 71 | 1 | 63, 64, 65 | 3 |
| Liver | Plethora of alveolar capillaries | 11, 12, 13, 14, 15 | 5 | 2, 3, 4, 5 | 4 | 71, 72, 73, 74, 75 | 5 | 61, 63, 64, 65 | 4 |
| | Plethora of veins | 11, 12, 13, 14, 15 | 5 | 2, 3, 4, 5 | 4 | 71, 72, 73, 74, 75 | 5 | 61, 63, 64, 65 | 4 |
| | Lymphoid infiltration of portal tracts | — | — | — | — | — | — | — | — |
| Kidney | Small foci of interchannel lymphoid infiltration | 12 | 1 | 1, 2 | 2 | — | — | 61 | 1 |
| | Plethora of veins | 11, 12, 13 | 3 | 3, 5 | 2 | 71, 72, 73 | 3 | 65 | 1 |

At autopsy after the withdrawal period of fullerene tris (aminocaproic acid) hydrate administration, the external examination and study did not show differences between the experimental and control group rats. No brown color of tissues at the sites of previous fullerene tris(aminocaproic acid) hydrate injections was found. In statistical analysis of the weight coefficients of organs, no significant difference was found between experimental and control animals (Table 25).

it was also concluded that the identified changes were not induced by the studied substance.

At the injection site of the test and control substances (the skeletal muscle), similar changes were observed in both experimental and control animals: few thin elongated areas of a completely formed dense fibrous connective tissue located either along the muscle fibers, or at an acute angle to them.

TABLE 25

Weight coefficients of organs in rats after the peroid of fullerene tris(aminocaproic acid) hydrate withdrawal

| Dose, mg/kg | Weight coefficients of viscera, g/kg body weight | | | | | | |
|---|---|---|---|---|---|---|---|
| | Heart | lungs | liver | Spleen | kidneys | thymus | Testicles |
| Males | | | | | | | |
| | $3.9 \pm 0.4$ | $7.5 \pm 1.9$ | $38.5 \pm 3.8$ | $4.8 \pm 0.6$ | $6.5 \pm 0.5$ | $1.7 \pm 0.3$ | $9.5 \pm 1.0$ |
| | $4.1 \pm 0.4$ | $7.1 \pm 0.5$ | $32.2 \pm 1.8$ | $5.2 \pm 0.7$ | $6.5 \pm 0.4$ | $1.2 \pm 0.4$ | $9.7 \pm 1.2$ |
| 9.0 | $4.0 \pm 0.6$ | $7.0 \pm 0.5$ | $38.6 \pm 4.0$ | $5.3 \pm 1.1$ | $7.1 \pm 0.4$ | $1.6 \pm 0.5$ | $9.8 \pm 1.0$ |
| 20.0 | $3.3 \pm 0.4$ | $7.8 \pm 0.6$ | $37.6 \pm 1.4$ | $5.1 \pm 0.6$ | $7.0 \pm 0.6$ | $1.3 \pm 0.5$ | $10.5 \pm 1.5$ |
| Females | | | | | | | |
| 0 | $3.7 \pm 0.4$ | $8.7 \pm 1.8$ | $35.0 \pm 4.2$ | $5.5 \pm 1.6$ | $6.7 \pm 0.7$ | $1.7 \pm 0.4$ | — |
| 3.0 | $3.5 \pm 0.7$ | $8.7 \pm 0.7$ | $33.9 \pm 3.9$ | $4.7 \pm 0.5$ | $7.2 \pm 0.5$ | $1.7 \pm 0.3$ | — |
| 9.0 | $4.1 \pm 0.3$ | $8.6 \pm 0.7$ | $36.9 \pm 2.0$ | $5.7 \pm 1.4$ | $8.0 \pm 1.1$ | $1.4 \pm 0.4$ | — |
| 20.0 | $3.8 \pm 0.9$ | $8.1 \pm 0.9$ | $38.2 \pm 3.8$ | $5.6 \pm 0.4$ | $6.8 \pm 0.2$ | $1.3 \pm 0.3$ | — |

A microscopic examination of histological samples of organs showed changes that were in character and severity mostly as described after the fullerene tris(aminocaproic acid) hydrate administration course and were intrinsic, approximately to the same extent, to both experimental and control group animals (Table 26). For this reason, in this case This morphological picture shows no difference in the speed and nature of the healing process at the injection sites of the solvent and fullerene tris(aminocaproic acid) hydrate.

Thus, as a result of a post mortem study, no morphological features were found to be associated with exposure to or withdrawal of fullerene tris(aminocaproic acid) hydrate.

TABLE 26

Results of microscopic examination of morphologic changes in organs and tissues of rats after the period of fullerene tris(aminocaproic acid) hydrate withdrawal

| Substance | | Solvent | | | | Fullerene tris(aminocaproic acid) | | | |
|---|---|---|---|---|---|---|---|---|---|
| Dose (mg/kg) | | 0 | | | | 20 | | | |
| Gender | | Males | | Females | | Males | | Females | |
| Number of animals in group | | 5 | | 5 | | 5 | | 5 | |
| Number of survivors | | 5 | | 5 | | 5 | | 5 | |
| Organ/ tissue | Morphological changes | Animals with changes | | | | | | | |
| | | Ind. No | Number | Ind. No | Number | Ind. No | Number | Ind. No | Number |
| Lung | Thickening of the interalveolar septa (total) | 17, 18, 20 | 3 | — | — | 79 | 1 | — | — |
| | Thickening of the interalveolar septa (sites) | 19 | 1 | 9 | 1 | 76, 77, 78, 80 | 4 | 66 | 1 |
| | Plethora of blood vessels | 16, 18, 19 | 3 | 6, 7, 8, 9, 10 | 5 | 76, 77, 78 | 3 | 66, 67, 68, 69, 70 | 5 |

TABLE 26-continued

Results of microscopic examination of morphologic changes in organs and tissues of rats after the period of fullerene tris(aminocaproic acid) hydrate withdrawal

| | | | | | | | | | | |
|---|---|---|---|---|---|---|---|---|---|---|
| | Plethora of alveolar capillaries | 18, 19 | 2 | 7, 8, 9 | 3 | — | — | 66, 70 | 2 |
| | Narrowing of the bronchial tubes | 17, 18, 19, 20 | 4 | — | — | 78, 79, 80 | 3 | — | — |
| | Areas of emphysematous expansion of alveoli | 17, 20 | 2 | — | — | — | — | — | — |
| | Perivascular lymphoid infiltration | — | — | 8 | 1 | — | — | 69 | 1 |
| Liver | Plethora of sinusoidal capillaries | 16, 17, 18, 19, 20 | 5 | 6, 7, 8, 9, 10 | 5 | 76, 77, 78, 79, 80 | 5 | 66, 67, 68, 69, 70 | 5 |
| | Plethora of veins | 16, 17, 18, 19, 20 | 5 | 6, 7, 8, 9, 10 | 5 | 76, 77, 78, 79, 80 | 5 | 66, 67, 68, 69, 70 | 5 |
| Kidney | Small foci of interchannel lymphoid infiltration | 16, 17, 18, 19 | 4 | 7, 9, 10 | 3 | 76, 77, 79, 80 | 4 | 70 | 1 |

Conclusion. Throughout the period of fullerene tris(aminocaproic acid) hydrate administration to rats and the period of withdrawal of the substance administration, there were no signs of change in the clinical condition of the animals. The administration of fullerene tris(aminocaproic acid) hydrate had no effect on the behavior, condition of the wool cover, the visible mucous membranes, and body weight gain in experimental animals.

A long-term (one-month) administration of fullerene tris(aminocaproic acid) hydrate to rats had no effect on peripheral blood values. Withdrawal of administration of the test substance likewise caused no changes in blood values.

After the end of fullerene tris(aminocaproic acid) hydrate administration, a reliable reduction of urea level within the physiological range at the maximal tested dose (20 mg/kg) was found in male rats, while in female rats, an insignificant but reliable increase in alanine amino transferase was found. A reduction in creatinine concentration at the maximal tested dose was shown after the end of the period of the tested substance in male and female rats.

In analyzing the results of rat urine studies after the period of fullerene tris(aminocaproic acid) hydrate withdrawal, a decrease in the relative density of urine in the female group at a dose of 20 mg/kg was noticed compared to control group animals.

As a result of post-mortem studies, no signs of a damaging effect of fullerene tris(aminocaproic acid) hydrate on rats body were found after one month of intramuscular administration at doses of 20 mg/kg body weight.

Thus, the studies showed no significant signs of a damaging effect of fullerene tris(aminocaproic acid) hydrate on rat's body either after 30 days of intramuscular administration at doses of up to 20 mg/kg body weight, or after the end of the withdrawal period.

Example 10

Acute Toxicity Studies of Fullerene Tris(Aminocaproic Acid) Hydrate in Laboratory Animals after a Single Intramuscular Injection The experiment was carried out at the Research Center for Toxicology and Hygienic Regulation on Bioagents (FGUN NITs TBP FMBA of Russia), the town of Serpukhov.

The tasks of these studies were to determine tolerable and toxic doses and to study a possible damaging effect of the substance on laboratory animals after intramuscular administration.

The experiments were carried out on Wistar non-pedigree white mice and rats purchased at the nursery of GU NTsBMT, the Russian Academy of Medical Sciences. The maintenance of animals met the sanitary regulations approved by the Ministry of Public Health of the USSR, Jul. 6, 1973, on the organization, equipment, and maintenance of experimental and biological clinics (vivariums). Animals were fed ad libitum with extruded mixed fodder PK-120-1, prepared according to GOST 50258-92. The animals were quarantined and acclimatized in a vivarium for at least 10 days.

Experimental animal groups were formed by random sampling taking the body weight as a leading indicator.

Solutions of the tested substance in 20% aqueous solution of DMSO to be injected to animals were prepared under aseptic conditions ex tempora. The solutions were packaged into appropriately labeled bottles and stored until administration at a temperature of 2 to 6° C. for no longer than for 2 hours.

The substance was administered to mice and rats intramuscularly in doses of 5, 50, and 500 mg/kg. The maximal tested doses were limited by the maximal permissible volumes for intramuscular injection to mice and rats. The animals of control groups were injected with 20% aqueous solution in the same amount as the maximal doses of the substance.

The dose amounts to be administered were corrected taking into account individual's body weight.

During the observation period (for 14 days following administration), the general condition of an animal was evaluated for its physical activity, food and water consumption, condition of wool and visible mucous membranes, and body weight.

After the end of the observation period, the mice and rats that received the substance in a dose of 500 mg/kg and the control substance (the solvent) were autopsied. Animals were euthanized by inhalation of carbon dioxide. Postmortem examination was performed within 1 hour after euthanasia. The morphological status of the viscera was determined visually at autopsy.

Statistical processing of the results was carried out by variation statistics methods using Student's test.

The results of studies. At all tested doses, no clinical symptoms of poisoning were observed in animals. No death occurred during the observation period; there was no difference in the general condition of animals between the experimental and control groups. Animals readily ate food and evenly gained weight; no statistically reliable differences were found between group-average body weight values in experimental groups relative to control groups (Table 27, 28).

TABLE 27

Body weights of mice

| Substance dose, mg/kg | Animal body weight, g (M ± SD) | | |
|---|---|---|---|
| | day 0 | day 7 | day 14 |
| males | | | |
| 0 (solvent) | 22.7 ± 1.4 | 24.3 ± 1 | 25.9 ± 1. |
| 5 | 23.0 ± 2.9 | 24.1 ± 2 | 25.4 ± 2. |
| 50 | 22.4 ± 2.1 | 23.7 ± 2 | 25.4 ± 2. |
| 500 | 22.6 ± 2.2 | 24.2 ± 1 | 26.2 ± 1. |
| females | | | |
| 0 (solvent) | 19.1 ± 1. | 20.8 ± 1 | 23.3 ± 1. |
| 5 | 19.1 ± 2. | 20.6 ± 2 | 22.8 ± 2. |
| 50 | 18.6 ± 1. | 19.9 ± | 21.9 ± 1. |
| 500 | 18.9 ± 1. | 20.7 ± 0 | 22.8 ± 1. |

The $LD_{50}$ of the substance for intramuscular administration to mice and rats of both genders exceeds the maximal tested dose (500 mg/kg).

TABLE 28

Body weights in rats

| Substance dose, mg/kg | Animal body weight, g (M ± SD) | | |
|---|---|---|---|
| | day 0 | day 7 | day 14 |
| Males | | | |
| 0 (solvent) | 187 ± 21.4 | 232 ± 30.5 | 283 ± 33.5 |
| 5 | 188 ± 12.5 | 228 ± 18.1 | 276 ± 17.8 |
| 50 | 190 ± 14.3 | 228 ± 17.0 | 279 ± 18.3 |
| 500 | 189 ± 14.1 | 207 ± 19.3 | 258 ± 24.1 |
| Females | | | |
| 0 | 162 ± 15.3 | 185 ± 17.4 | 212 ± 20.6 |
| 5 | 163 ± 15.5 | 183 ± 15.0 | 206 ± 17.0 |
| 50 | 165 ± 17.5 | 177 ± 17.5 | 201 ± 15.8 |
| 500 | 160 ± 8.1 | 169 ± 8.0 | 198 ± 10.3 |

Autopsy was performed in mice and rats 14 days after a single intramuscular injection of the substance. Inasmuch as no death was observed in any group of animals during the observation period regardless of the dose administered, only those mice and rats that received the substance at the maximum dose (500 mg/kg) were subjected to necropsy, as well as animals from control groups. Animals were euthanized by inhalation of carbon dioxide.

In external examination of mice and rats in the experimental and control groups, the general picture was noted: wool cover was smooth and shiny; skin was elastic and mobile; subcutaneous tissue was moderate; the visible mucous membrane was pale, without ulceration and foreign overlays; and abnormal discharge from the body's orifices were absent.

Autopsy likewise did not show differences between mice and rats in all experimental and control groups. The organs of chest and abdominal cavities had anatomically correct position and normal macrostructure; none pathological changes were found. At the site of injection of the substance (femoris), no signs of lesion were detected.

Thus, post mortem examination has not detected signs of a damaging effect of the substance after a single intramuscular administration to mice and rats at doses up to 500 mg/kg.

Conclusion. All of the tested doses of the substance have been found to not cause intoxication and death of experimental animals. The $LD_{50}$ values of fullerene tris(aminocaproic acid) hydrate for mice and rats exceed the maximal tested dose (500 mg/kg) and thereby exceed the maximal one-time therapeutic human dose (2.9 mg/kg) by a factor of more than 170.

Species and gender differences in sensitivity to the substance in doses up to 170 equitherapeutic doses have not been found. The substance does not cause a local irritant effect after a single intramuscular injection.

Thus, fullerene tris(aminocaproic acid) hydrate has a high therapeutic index and can cause poisoning from accidental overdose.

The invention claimed is:

1. A method for producing hydrated N-fullerene amino acids of general formula $C_{60}(H)_3\{NH(CH_2)_n COOH\}_3 \cdot xH_2O$, wherein $C_{60}$ is fullerene; n=5, 6, or 7; and x=8 to 10, the method comprising the steps of reacting fullerene with a 15-fold molar excess of anhydrous potassium salts of amino acids of general form $NH_2(CH_2)_n COOH$, wherein n=5, 6, or 7, in an aromatic solvent medium, comprising a slow addition to a resulting suspension of a phase-transfer catalyst under stirring and heating to temperature not higher than 60 to 80° C. to form a solution that is completely decolorized and a solid residue, wherein said residue comprises potassium salts of resulting fullerene amino acid derivatives, followed by separating said residue and dissolving in water to obtain a 0.8 M aqueous solution which is then treated with a 0.1 N solution of an organic or mineral acid, then followed by centrifuging, washing, and drying the residue.

2. The method according to claim 1, wherein the anhydrous potassium salts of amino acids are in a finely dispersed state and separating of the reside is carried out by filtering, ethanol washing, and drying.

3. The method according to claim 1, wherein the phase-transfer catalyst is a methyl polyethylene glycol ester having a molecular weight of 400 or 500.

4. The method according to claim 2, wherein the phase-transfer catalyst is a methyl polyethylene glycol ester having a molecular weight of 400 or 500.

* * * * *